(12) United States Patent
Abdou

(10) Patent No.: US 7,641,690 B2
(45) Date of Patent: Jan. 5, 2010

(54) BONE FIXATION AND FUSION DEVICE

(76) Inventor: M. Samy Abdou, 7790 Doug Hill, San Diego, CA (US) 92127

( * ) Notice: Subject to any disclaimer, the term of this patent is extended or adjusted under 35 U.S.C. 154(b) by 134 days.

(21) Appl. No.: 11/211,160

(22) Filed: Aug. 23, 2005

(65) Prior Publication Data

US 2006/0074488 A1 Apr. 6, 2006

Related U.S. Application Data

(60) Provisional application No. 60/603,809, filed on Aug. 23, 2004, provisional application No. 60/670,898, filed on Apr. 8, 2005, provisional application No. 60/670,899, filed on Apr. 8, 2005, provisional application No. 60/670,900, filed on Apr. 8, 2005.

(51) Int. Cl.
*A61F 2/44* (2006.01)
(52) U.S. Cl. .................................... 623/17.11
(58) Field of Classification Search ............. 623/17.11, 623/17.12, 17.13, 17.15, 17.16
See application file for complete search history.

(56) References Cited

U.S. PATENT DOCUMENTS

| | | | |
|---|---|---|---|
| 4,289,123 A | 9/1981 | Dunn | |
| 5,133,717 A | 7/1992 | Chopin | |
| 5,545,164 A | 8/1996 | Howland | |
| 5,616,142 A | 4/1997 | Yuan et al. | 606/61 |
| 5,681,311 A | 10/1997 | Foley et al. | 606/61 |
| 5,928,233 A | 7/1999 | Apfelbaum et al. | |
| 5,993,449 A | 11/1999 | Schlapfer et al. | 606/60 |
| 6,039,761 A * | 3/2000 | Li et al. | 623/17.16 |
| 6,159,244 A | 12/2000 | Suddaby | |
| 6,193,757 B1 * | 2/2001 | Foley et al. | 623/17.16 |
| 6,306,136 B1 | 10/2001 | Beccelli | 606/61 |
| 6,524,315 B1 | 2/2003 | Selvitelli et al. | |
| 6,547,790 B2 | 4/2003 | Harckey, III et al. | |
| 6,599,295 B1 | 7/2003 | Tornier et al. | |
| 7,232,463 B2 * | 6/2007 | Falahee | 623/17.11 |
| 2002/0055741 A1 | 5/2002 | Schlapfer et al. | 606/71 |
| 2002/0099386 A1 | 7/2002 | Beger et al. | |
| 2002/0183755 A1 | 12/2002 | Michelson et al. | |
| 2003/0018389 A1 | 1/2003 | Castro et al. | |
| 2003/0078583 A1 | 4/2003 | Biedermann et al. | 606/69 |
| 2004/0133207 A1 | 7/2004 | Abdou | 606/73 |
| 2004/0204713 A1 | 10/2004 | Abdou | 606/71 |
| 2005/0004573 A1 | 1/2005 | Abdou | 606/61 |

(Continued)

FOREIGN PATENT DOCUMENTS

WO 2004/032726 4/2004

(Continued)

*Primary Examiner*—Corrine M McDermott
*Assistant Examiner*—Christopher D Prone
(74) *Attorney, Agent, or Firm*—Fred C. Hernandez; Mintz, Levin, Cohn, Ferris, Glovsky and Popeo P.C.

(57) ABSTRACT

Disclosed is a bone fusion cage that contains bone graft and is implanted between bones in a skeletal system. The cage bears structural loads that are transmitted through the bones of the skeletal system and at least partially shields the contained bone graft from the structural loads. The cage is configured to provide a secondary load to the bone graft independent of the structural load to promote fusion of the bone graft to adjacent bones.

18 Claims, 33 Drawing Sheets

U.S. PATENT DOCUMENTS

| | | |
|---|---|---|
| 2005/0021040 A1 | 1/2005 | Bertagnoli |
| 2005/0119747 A1 | 6/2005 | Fabris Monterumici et al. |
| 2005/0177163 A1 | 8/2005 | Abdou ........................ 606/72 |
| 2005/0273120 A1 | 12/2005 | Abdou |
| 2005/0288669 A1 | 12/2005 | Abdou |
| 2006/0149278 A1 | 7/2006 | Abdou |
| 2006/0217710 A1 | 9/2006 | Abdou |
| 2006/0229615 A1 | 10/2006 | Abdou |
| 2007/0093828 A1 | 4/2007 | Abdou |
| 2007/0106383 A1 | 5/2007 | Abdou |
| 2007/0123884 A1 | 5/2007 | Abdou |

FOREIGN PATENT DOCUMENTS

| | | |
|---|---|---|
| WO | 2004/062482 | 7/2004 |
| WO | 2004/093702 | 11/2004 |
| WO | WO 2005/122922 | 12/2005 |
| WO | WO 2006/041963 | 4/2006 |
| WO | WO 2006/058221 | 6/2006 |
| WO | WO 2006/089292 | 8/2006 |
| WO | WO 2006/096756 | 9/2006 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |

* cited by examiner

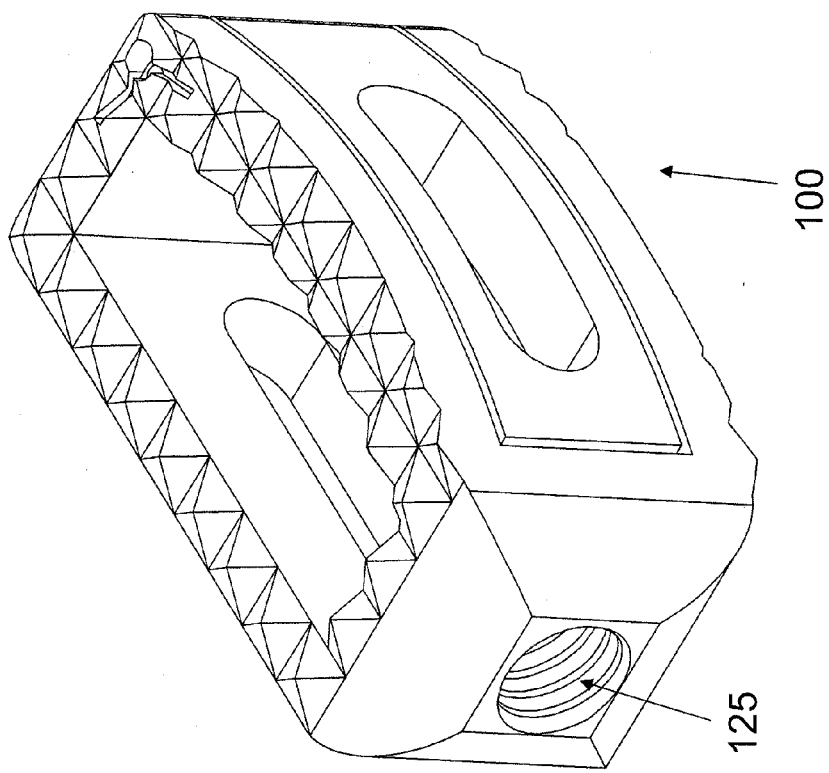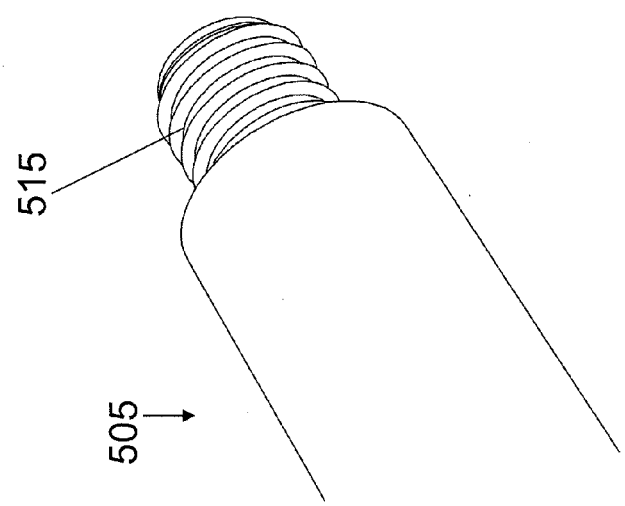
Fig. 6

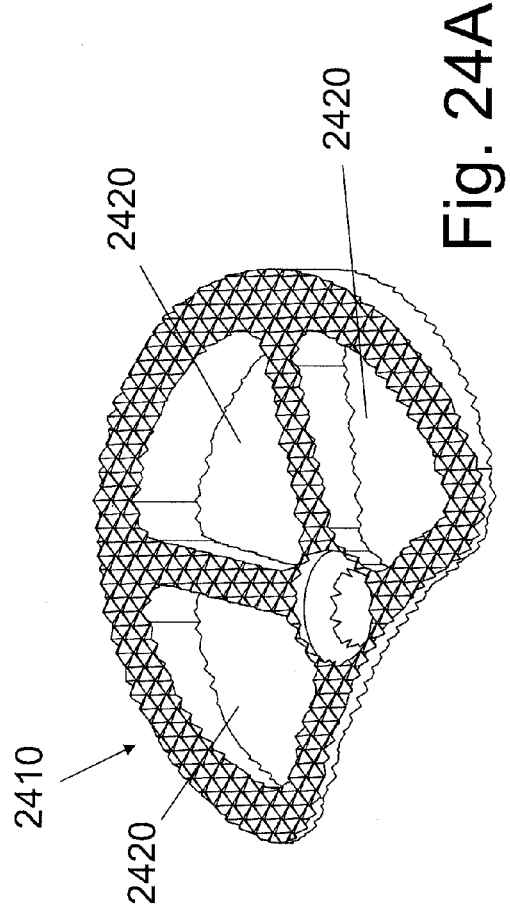
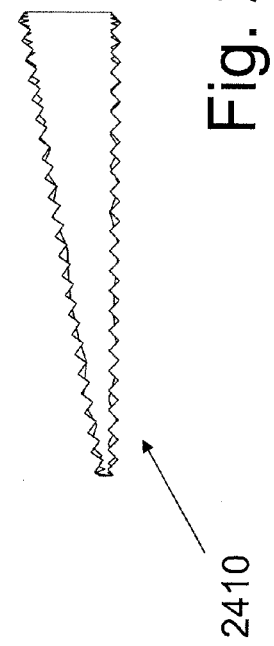
Fig. 24
Fig. 24A
Fig. 24B

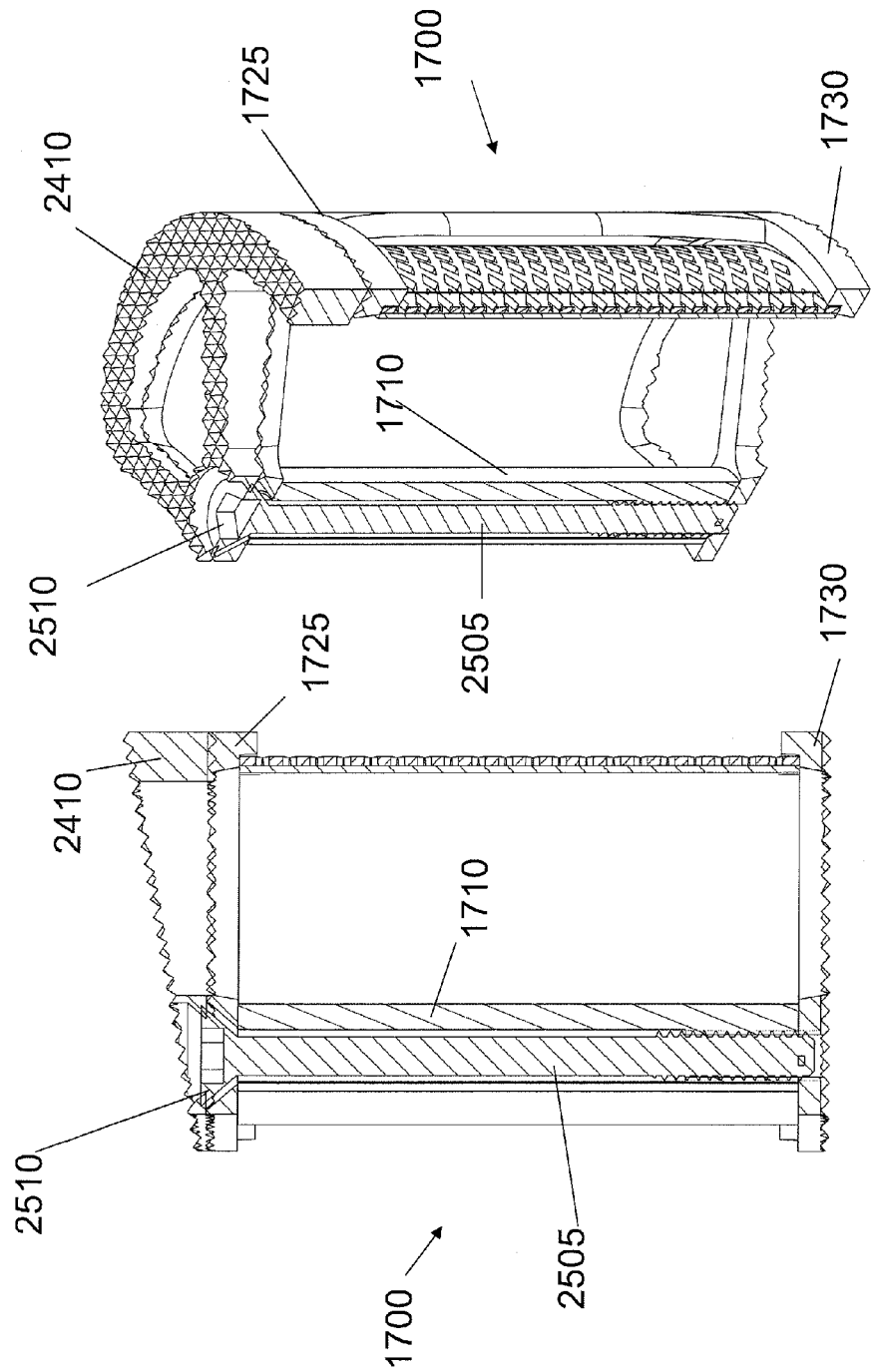

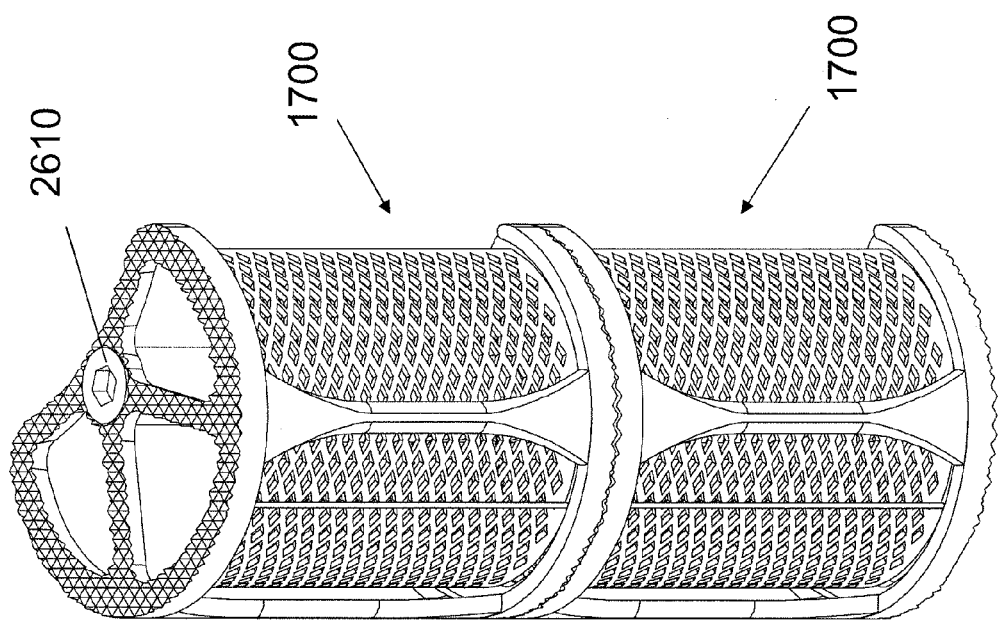

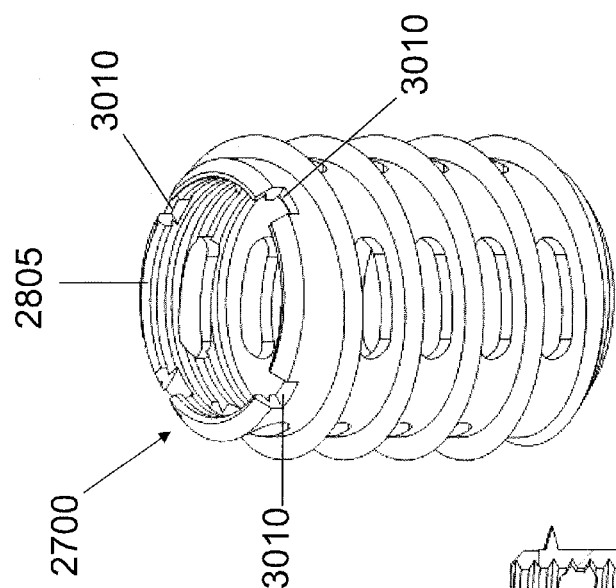
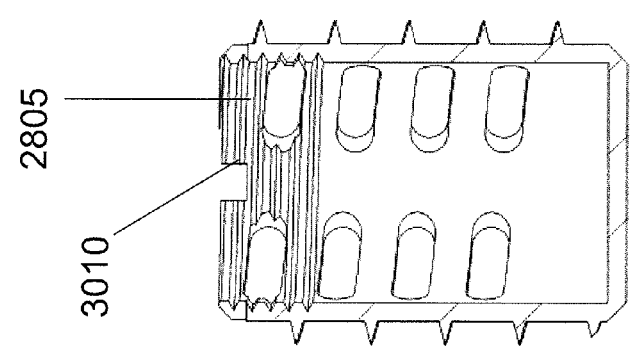
Fig. 27
Fig. 28

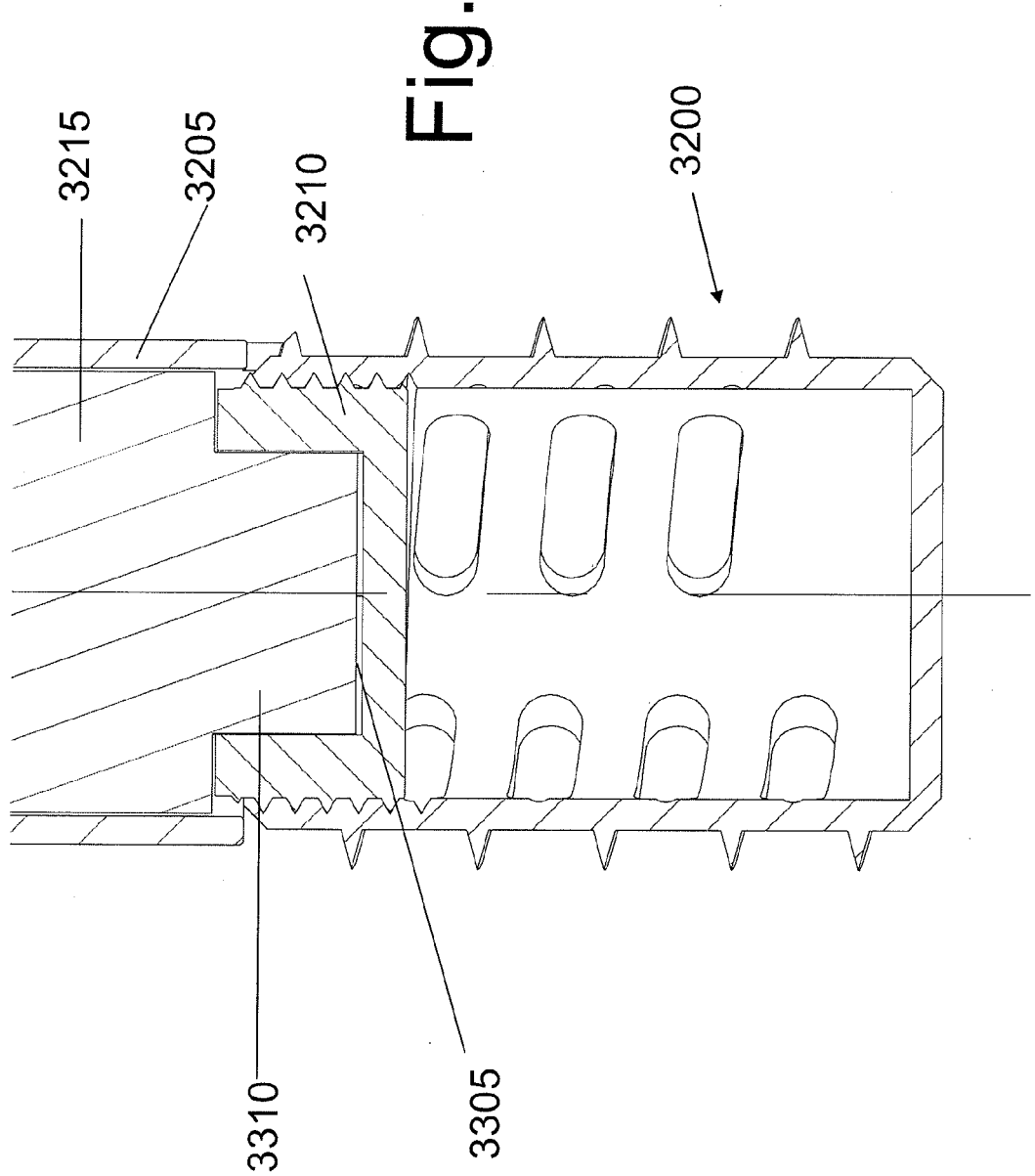

BONE FIXATION AND FUSION DEVICE

REFERENCE TO PRIORITY DOCUMENT

This application claims priority of the following co-pending U.S. Provisional Patent Applications: (1) U.S. Provisional Patent Application Ser. No. 60/603,809, filed Aug. 23, 2004; (2) U.S. Provisional Patent Application Ser. No. 60/670,898, filed Apr. 8, 2005; (3) U.S. Provisional Patent Application Ser. No. 60/670,899, filed Apr. 8, 2005; (4) U.S. Provisional Patent Application Ser. No. 60/670,900, filed Apr. 8, 2005. Priority of the aforementioned filing dates is hereby claimed, and the disclosures of the Provisional Patent Applications are hereby incorporated by reference in their entirety.

BACKGROUND

The present disclosure is directed at skeletal bone fixation systems, components thereof, and methods of implant placement. These devices are used during the surgical reconstruction of skeletal segments to bridge bony gaps and to adjust, align and fixate the remaining bone or bony fragments.

Whether for degenerative disease, traumatic disruption, infection or neoplastic invasion, the surgical resection of bone and the subsequent reconstruction of the skeletal segment is a common procedure in current medical practice. Regardless of the anatomical region or the specifics of the individual operation, many surgeons employ an implantable device to bridge the region of bone resection and provide structural support for the remaining skeletal segment. These devices are especially useful in spinal surgery where they are used to restore spinal alignment and to stabilize the spinal column after vertebral and/or disc resection.

While these devices provide immediate structural support of the operative segment, long term stability requires that a bone graft be used to replace the resected bone and that the grafted bone successfully incorporate ("fuse") within the skeletal segment. For these reason, many devices are designed with a rigid outer structure that is intended to provide immediate stability and a hollow central cavity that is used to retain the bone graft while the bony fusion proceeds.

Unfortunately, this design has a central flaw. In providing stability, the rigid outer structure bears the load transmitted through that skeletal segment and effectively shields the bone graft from stress forces. Since bone fusion occurs most effectively when the healing bone is subjected to load, placement of the graft within the device effectively shields it from stress forces and leads to a significant reduction in the likelihood of bony fusion. In addition, stress shielding will also significantly diminish the quality and density of the fusion mass that will eventually develop.

SUMMARY

In view of the proceeding, it would be desirable to design a fusion device without this significant limitation. The new device should provide both rigid support of the reconstructed segment as well as a reliable load on the bone graft. This would serve to maximize the likelihood of bony fusion and optimize the bone quality of the fusion mass.

Disclosed is a fusion device that is especially adapted for the reconstruction of the spinal column. In one aspect, the device comprises a rigid rectangular body which contains multiple openings. When implanted between two vertebral bodies, the upper end segment abuts the lower surface of the upper vertebra while the lower end segment abuts the upper surface of the lower vertebra. Each end segment has one or more central holes that permit contact between the vertebral surface and the bony fragments within the device center. The cage body provides structural support for the spinal segment.

The cage has one or more sides that can accommodate a movable side wall. The side wall is positioned within the open portion of the cage and a spring-loaded hinge is placed through the cage and into the side wall. The spring retains the side wall in the closed position.

The cage is threaded onto an insertion handle. The handle is used to deliver the cage into the operative site and also acts to hold the movable side-wall in the open position. Bone fragments are then packed into the cage center, the cage is placed into the operative site and the handle is removed. The memory inherent in the spring-loaded hinge will maintain a constant inward force applied to the healing bone fragments.

The bone fragments within the cage are pushed inwards in a horizontal plane and towards the two end segments in a longitudinal plane. The longitudinal component of the force increases the extent of contact between the bone graft and the vertebral surfaces whereas both components apply a constant force onto the graft. Both of these factors act synergistically to maximize the likelihood of bony fusion and optimize the quality of the fusion mass.

In another aspect, the fusion cage includes an upper segment, a lower segment, and a screen that collectively define an interior cavity. The cage supports a structural load that to the segment of the skeletal system in which the bones are located. The screen is configured to expand outward over a space. The interior cavity can be packed with bone graft sufficient to cause the screen to expand outwardly over the space. When packed with bone graft, the screen exerts a secondary force on the bone graft.

In another aspect, there is disclosed a bone fusion system, comprising a body sized and shaped for implanting between bones of a skeletal system and a load member. The body defines an internal cavity configured to contain bone graft, wherein the body supports a structural load transmitted through the bones when implanted in the skeletal system. The load member that exerts a secondary load onto bone graft contained within the internal cavity of the body.

In another aspect, there is disclosed a bone fusion system, comprising a cage for implanting between bones of a skeletal system. The cage defines an internal cavity for containing bone graft to be fused with the bones. The cage is configured to bear structural loads transmitted through the skeletal system, wherein at least a portion of the cage is configured to exert a secondary load to the bone graft contained within the internal cavity. The secondary load is separate from the structural load.

In another aspect, there is disclosed a method of fusing a pair of bones in a skeletal system, comprising: implanting a cage between the pair of bones such that the cage bears structural loads transmitted through the bones; packing the cage with bone graft, wherein the cage at least partially shields the bone graft from the structural loads; and causing the cage to exert a secondary load to the bone graft contained within the cage.

In another aspect, there is disclosed a bone fusion system, comprising a cage for implanting between bones of a skeletal system. The cage defines an internal cavity for containing bone graft to be fused with the bones. The cage is configured to bear structural loads transmitted through the skeletal system, wherein the cage is configured to subdivide the structural load at least by subsidence and exert a secondary load onto the bone graft contained within the internal cavity.

In another aspect, there is disclosed a method of fusing a pair of bones in a skeletal system, comprising: Inserting a cage between a pair of bones; exerting a load onto bone graft contained within an interior cavity of a fusion cage by advancing an instrument into the interior cavity at the time of cage insertion to compact, compress and load the bone graft.

The fusion cage device described herein provides rigid support of the reconstructed segment and reliable loading of the bone fragments within the cage. These and other features will become more apparent from the following description and certain modifications thereof when taken with the accompanying drawings.

BRIEF DESCRIPTION OF THE DRAWINGS

FIG. 6 shows an enlarged view of an insertion member positioned adjacent the borehole of the cage prior to coupling the insertion member to the cage.

FIG. 24A shows a perspective view of a wedge segment that can be placed against the upper or lower segments so as to achieve an inclined surface.

FIG. 24B shows a side, cross-sectional view of the wedge segment.

FIG. 25A shows a side, cross-sectional view of the cage with the wedge segment attached.

FIG. 25B shows a perspective, cross-sectional view of the cage with the wedge segment attached.

FIG. 26 shows a pair of cages positioned atop one another.

FIG. 27 shows yet another embodiment of a fusion cage.

FIG. 28 shows a cross-sectional view of the fusion cage of FIG. 27.

FIG. 34 shows a cross-sectional view of the cage coupled to the insertion/load system.

DETAILED DESCRIPTION

Disclosed are methods and devices that are adapted to assist in the fusion of adjacent bones of a skeletal system. The methods and devices are described herein in the context of use in the spine, although the disclosed methods and devices are suitable for use in any skeletal region.

The device can be, for example, a cage configured to contain bone graft that fuses to one or more adjacent bones of a skeletal system in which the bones are located. The cage also provides structural support to the segment of the skeletal system in which the bones are located. In this regard, the cage bears the structural load that is transmitted through the skeletal segment to at least partially shield the contained bone graft from the structural load. However, the cage is configured to provide a secondary load (separate from the structural load) to the bone graft contained within the cage, wherein the secondary load promotes fusion between the bone graft and adjacent bone of the skeletal system. The secondary load contributes to an advantageous increase in density of the fusion mass that develops as the bony fusion between the bone graft and adjacent bone proceeds. The secondary load is at least partially independent of the structural load transmitted through the skeletal system that the cage supports.

The cage can also be configured to exert at least a portion of the secondary load to the bones of the skeletal system adjacent the cage. The cage can further be configured so that at least a portion of the structural load is applied to the bone graft contained within the cage. In this regard, for example, the cage can subdivide the structural load by subsidence of adjacent bones and exert the secondary load onto the bone graft contained within the cage. The cage can also be configured to facilitate surface contact between the bone graft within the cage and the neighboring native bone.

Figure 1:
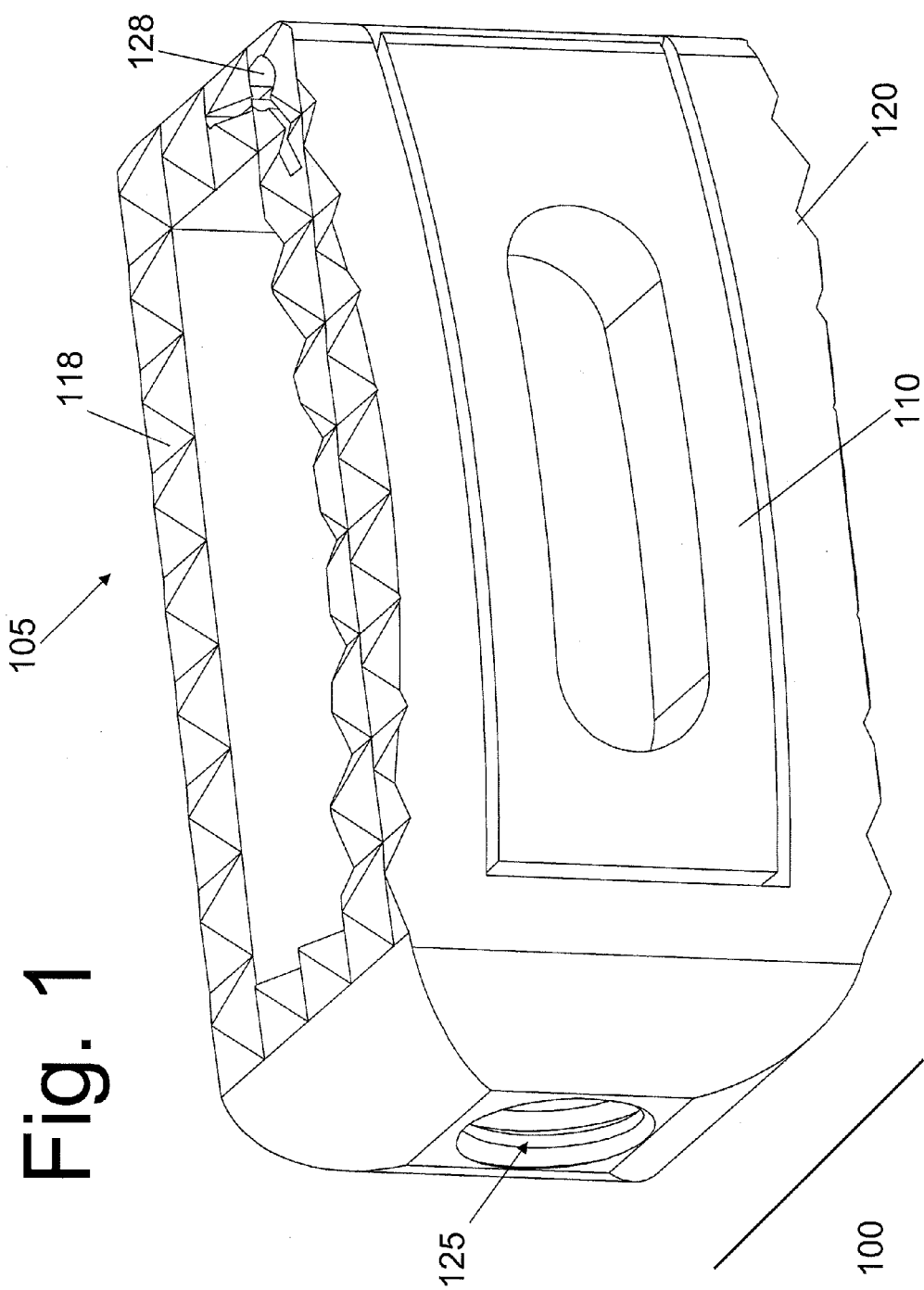
FIG. 1 shows a perspective view of a first embodiment of a cage in an assembled state.
Figure 2:
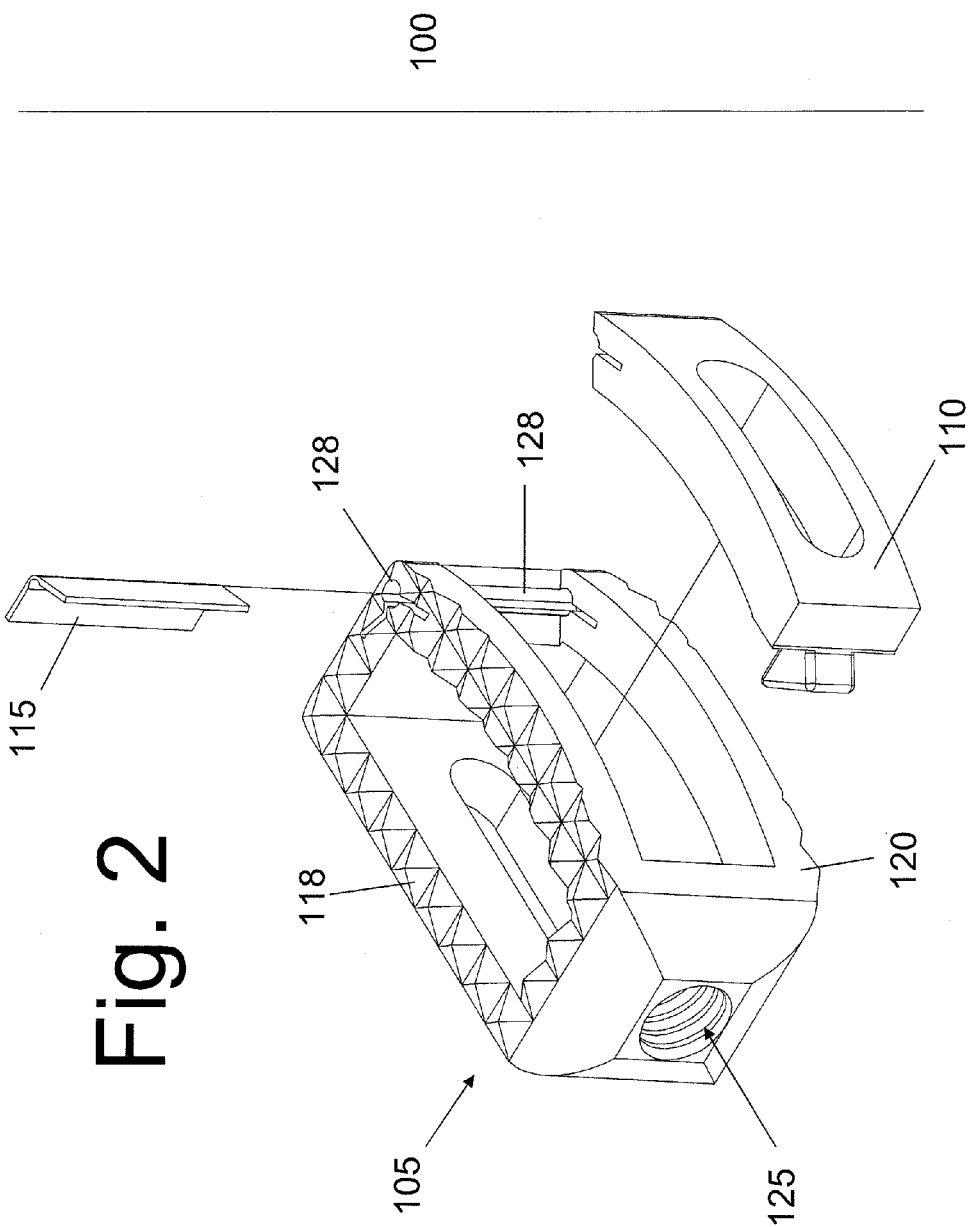
FIG. 2 shows a perspective view of the cage in an exploded state.

FIG. 1 shows a perspective view of a first embodiment of a cage 100 in an assembled state and FIG. 2 shows a perspective view of the cage 100 in an exploded state. The cage 100 is sized and shaped to be implanted between an upper vertebra and a lower vertebra of a spine.

The cage 100 includes a main body 105 configured to contain bone graft, at least one load member 110 that provides a load to the contained bone graft, and a hinge 115 (shown in FIG. 2) that couples the load member 110 to the main body 105. The cage 100 is configured to be implanted between a pair of bones, such as vertebrae, so as to provide structural support and encourage fusion between the bones and bone graft contained within the cage 100. As mentioned, the cage 100 is described herein in an exemplary embodiment where the cage is positioned between two vertebrae, although it should be appreciated that the cage 100 can be used with other bones in a skeletal system.

With reference to FIGS. 1 and 2, the main body 105 has a structure that is configured to contain bone graft and to be implanted between a pair of vertebrae. The main body 105 can be rectangular-shaped and is made of a rigid material, such as carbon fiber. The rigidity of the main body 105 permits it to provide structural support to the spinal segment in which it is implanted.

The main body 105 defines an interior cavity that is at least partially exposed via one or more holes or openings disposed in the main body 105, such as on its sides, tops, and/or bottoms. The openings permit contact between the vertebral surfaces and the bone graft contained within the main body 105. One of the openings is sized and shaped to receive at least a portion of the load member 110, as described below.

The main body 105 has an upper region that defines an upper engagement surface 18 that contacts the upper vertebra when the cage is implanted between the vertebrae. The main body 105 further includes a lower region that defines a lower engagement surface 120. The upper and lower engagement surfaces 118, 120 can be flat or can have or regular or irregular-shaped structures thereon, such as having knurled or pyramidal structures as shown in FIGS. 1 and 2.

A borehole 125 extends through the main body, such as through one of its side walls. The borehole 125 is sized and shaped to receive an insertion member, as described in detail below. The borehole 125 can have internal threads that couple to corresponding threads on the insertion member.

In the embodiment shown in FIGS. 1 and 2, the load member 110 is a moveable side wall that is shaped to complement the shape of the opening in the side of the main body 105. The load member 110 can move in and out of the opening, such as in a rotating or pivoting manner, for example. In the embodiment shown in FIGS. 1 and 2, the load member 110 is door-like and has a substantially rectangular shape that complements the shape of the hole in the main body 105. However, the load member 110 can have other shapes and structures that are configured to provide a load to bone graft contained within the main body 105, as described in other embodiments below for example. The load member 110 can also be integrally formed with the main body 105.

As mentioned, the load member 110 is door-like such that it rotatably moves in and out of the opening in the side of the main body 105. In this regard, the load member 110 is coupled to the main body 105 via the hinge 115, which is positioned in a complementary-shaped slot 128 in the main body 105. A portion of the load member 110 is sized and shaped to mate with the slot 128 such that the hinge 115 rotatably retains the load member to the main body 110.

The hinge 115 provides a biasing force that biases the load member 110 towards a closed position wherein the load member 110 can apply a load to bone graft contained within the main body 105. The hinge can be made of any suitable material and can have any structure and shape that permits the hinge 115 to provide such a biasing force. In an exemplary embodiment, the hinge 115 is made of a thin titanium band that can serve as a spring for biasing the load member 110 toward the main body. The thin titanium band can also as a radio-opaque marker that can be used to ascertain the cage position on an x-ray.

Figure 3:
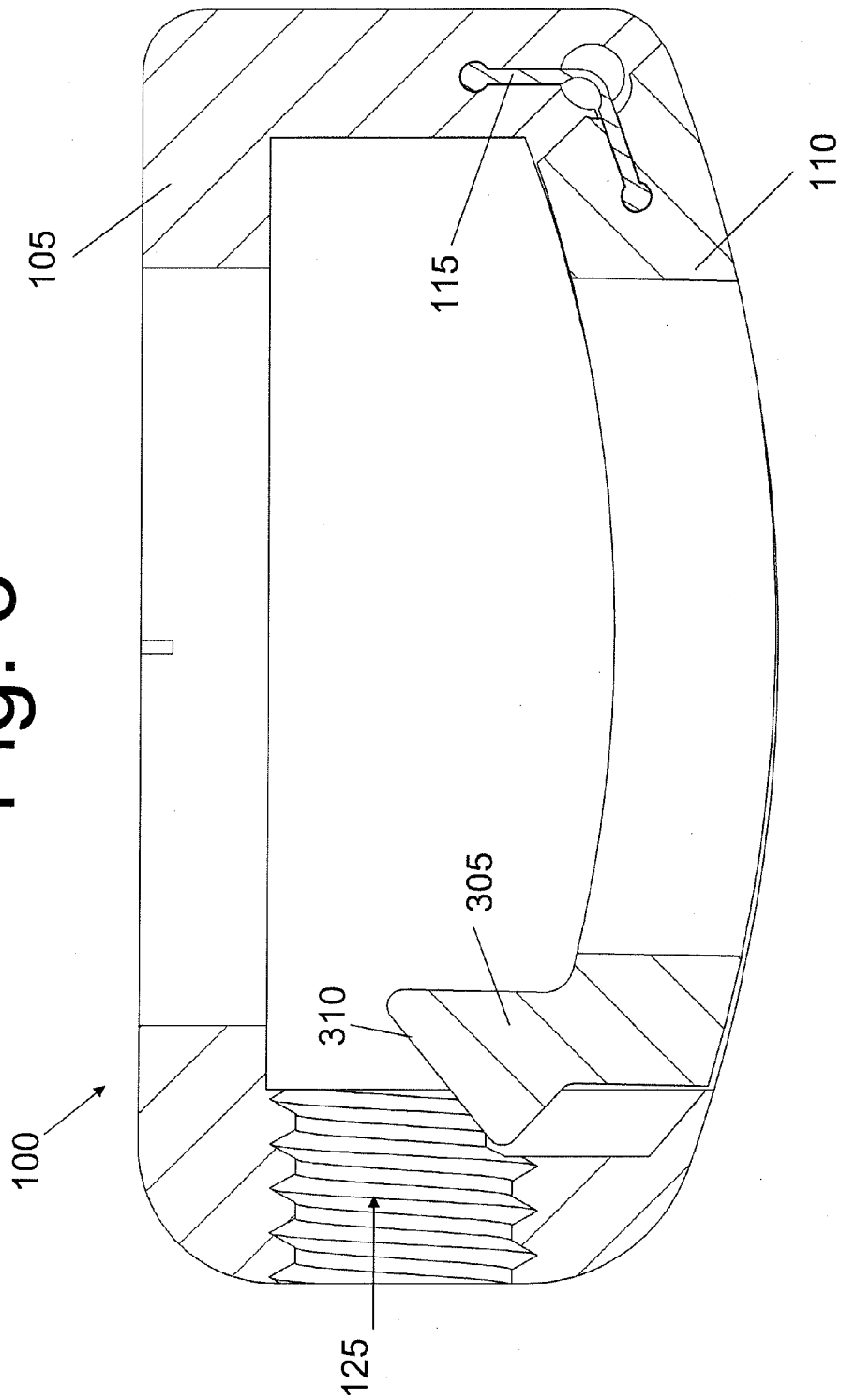
FIG. 3 shows a cross-sectional, plan view of the cage with the load member in a closed position.
Figure 4:
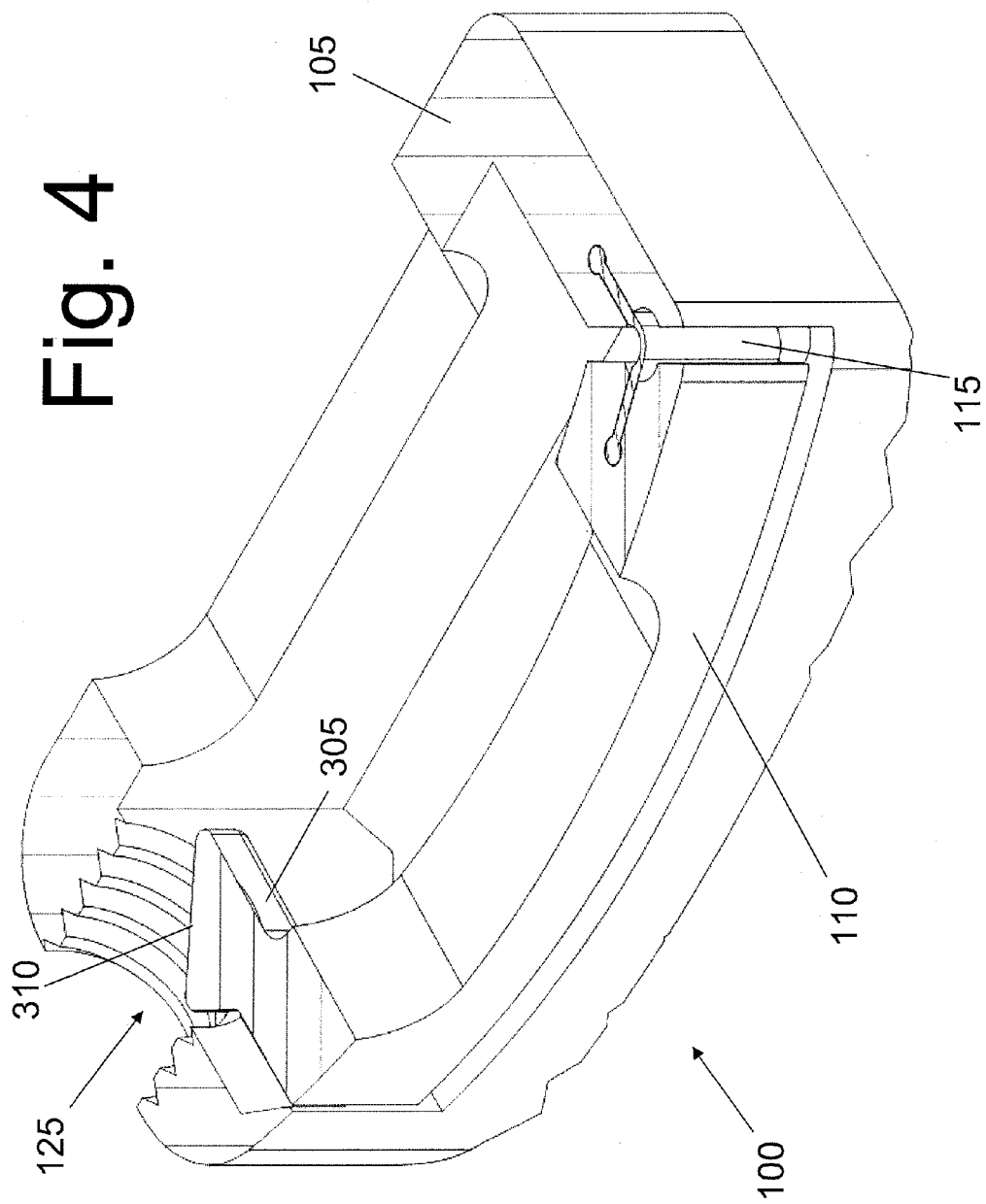
FIG. 4 shows a cross-sectional, perspective view of the cage with the load member in the closed position.

FIG. 3 shows a cross-sectional, plan view of the cage 100 with the load member 110 in a closed position. FIG. 4 shows a cross-sectional, perspective view of the cage 100 with the load member 110 in the closed position. The illustrated embodiment of the load member 110 includes a projection 305 that extends at least partially into the path of the borehole 125 when the load member is in the closed position. The projection 305 forms an abutment surface 310 that is inclined with respect to the axis of the borehole 125. The projection 305 can be used in combination with an insertion member to move the load member 110 to an open position, as described below.

At least a portion of the load member 110 extends into the internal cavity of the main body 105 for applying a load to at least a portion of the bone graft contained within the main body 105. The load can be applied by direct or indirect contact between at least a portion of the load member 110 and the contained bone graft, as described below.

Figure 5:
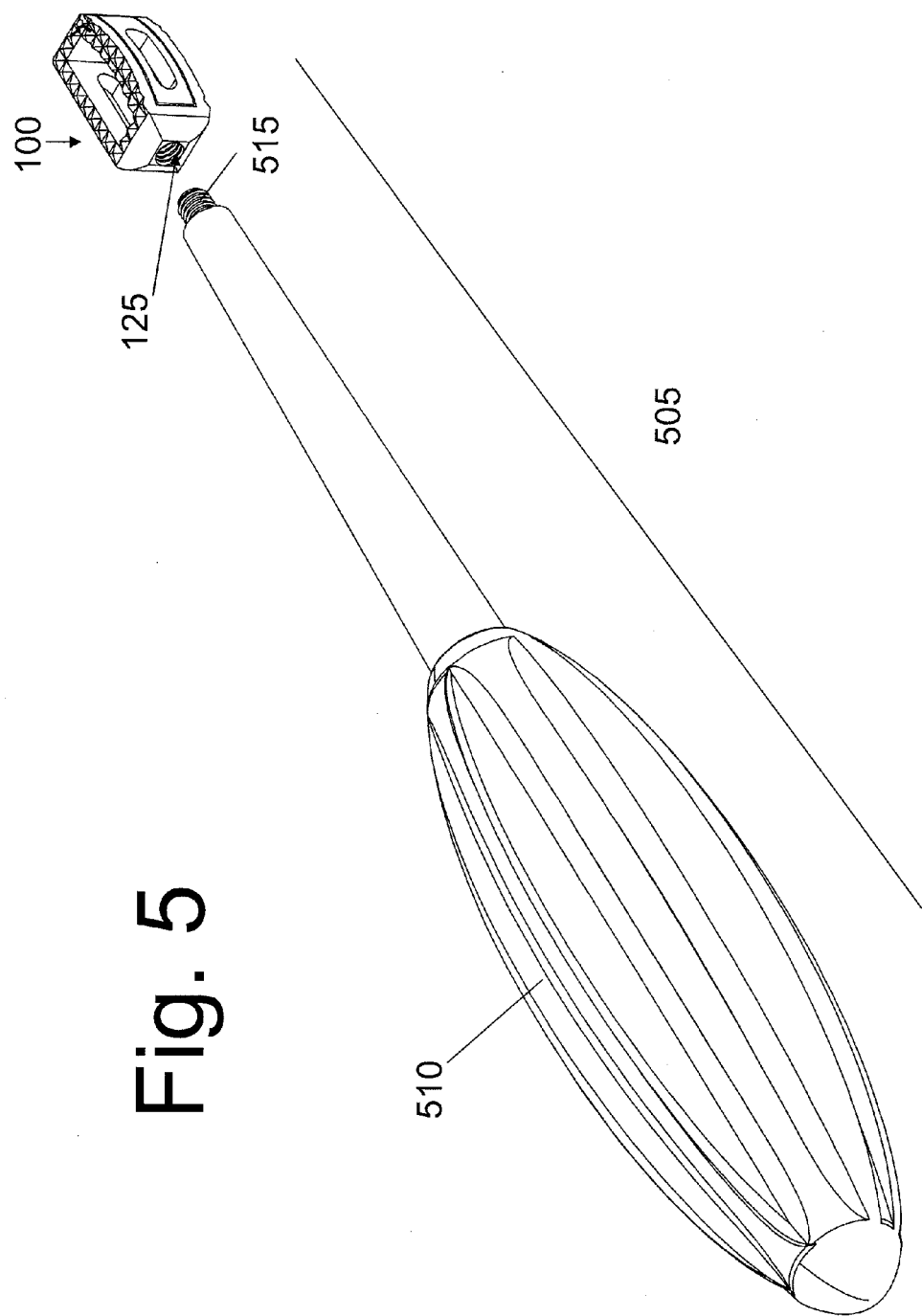
FIG. 5 shows a perspective view of an insertion member positioned adjacent the cage.

FIG. 5 shows a perspective view of an insertion member 505 positioned adjacent the cage 100. The insertion member 505 includes an elongate rod having a handle 510 on one end and a cage interface 515 on an opposite end. The cage interface 515 is configured to removably attach to the cage 515. In an exemplary embodiment, the cage interface 515 is a threaded end portion that removably mates with the threaded borehole 125 in the cage 100. FIG. 6 shows an enlarged view of the cage interface 515 of the insertion member 505 positioned adjacent the borehole 125 of the cage 100 prior to coupling the insertion member 505 to the cage 100.

Figure 7:
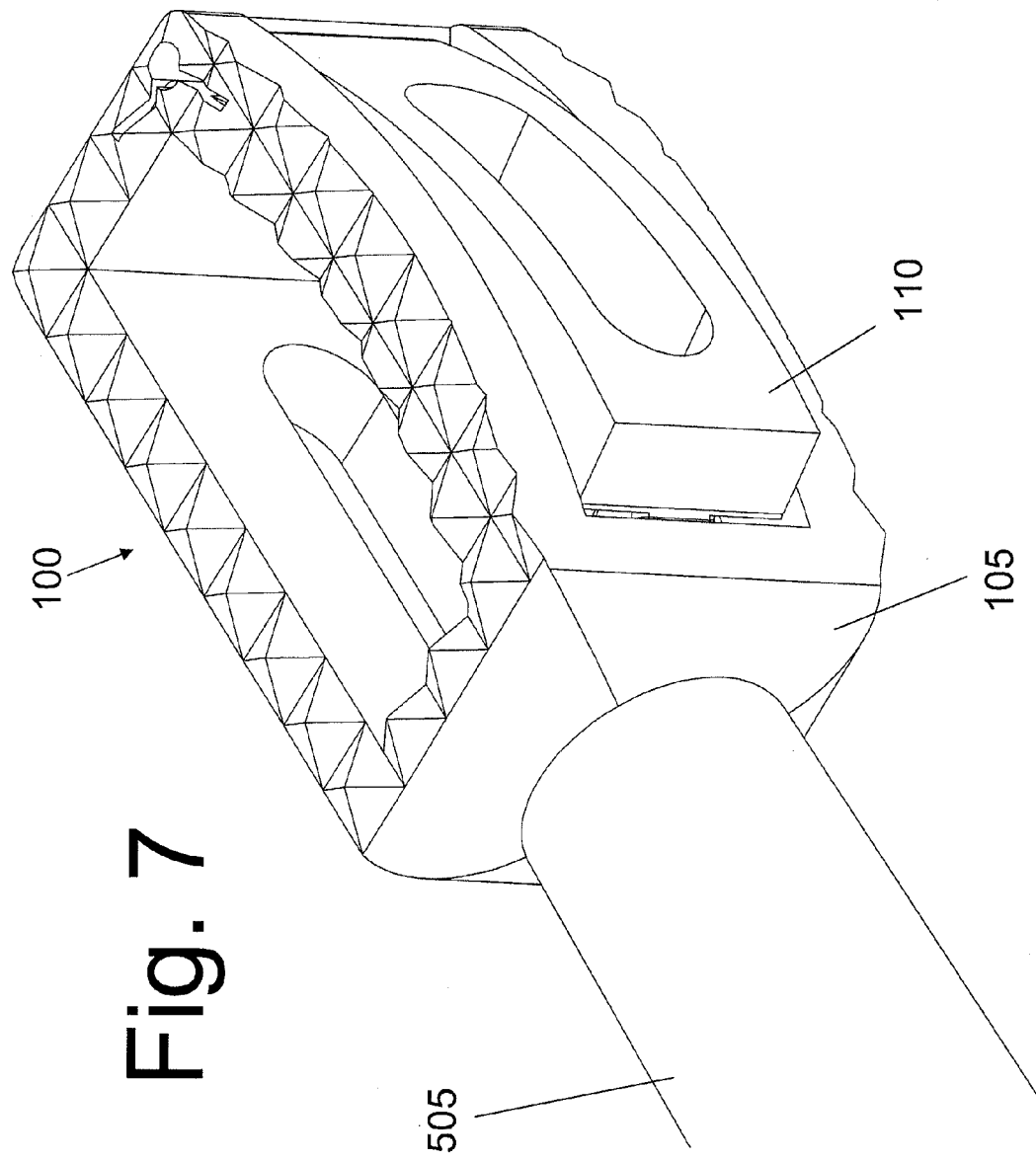
FIG. 7 shows an enlarged perspective view of a cage insertion member coupled to the cage.

The cage interface 515 of the insertion member 505 is threaded into the borehole 125 such that the cage interface 515 gradually moves further into the borehole 125. As the cage interface 515 moves further into the borehole 125, the cage interface 515 forces the load member 110 to move from the closed position (shown for example in FIG. 6) into an open position. In the open position, the load member is withdrawn at least partially from the main body 105. FIG. 7 shows an enlarged, perspective view of the insertion member 505 coupled to the cage 100 with the load member 110 in an open position. Note that the in the open position load member 110 is at least partially withdrawn from the main body 105 versus the closed position (shown in FIG. 6) where the.

Figure 8:
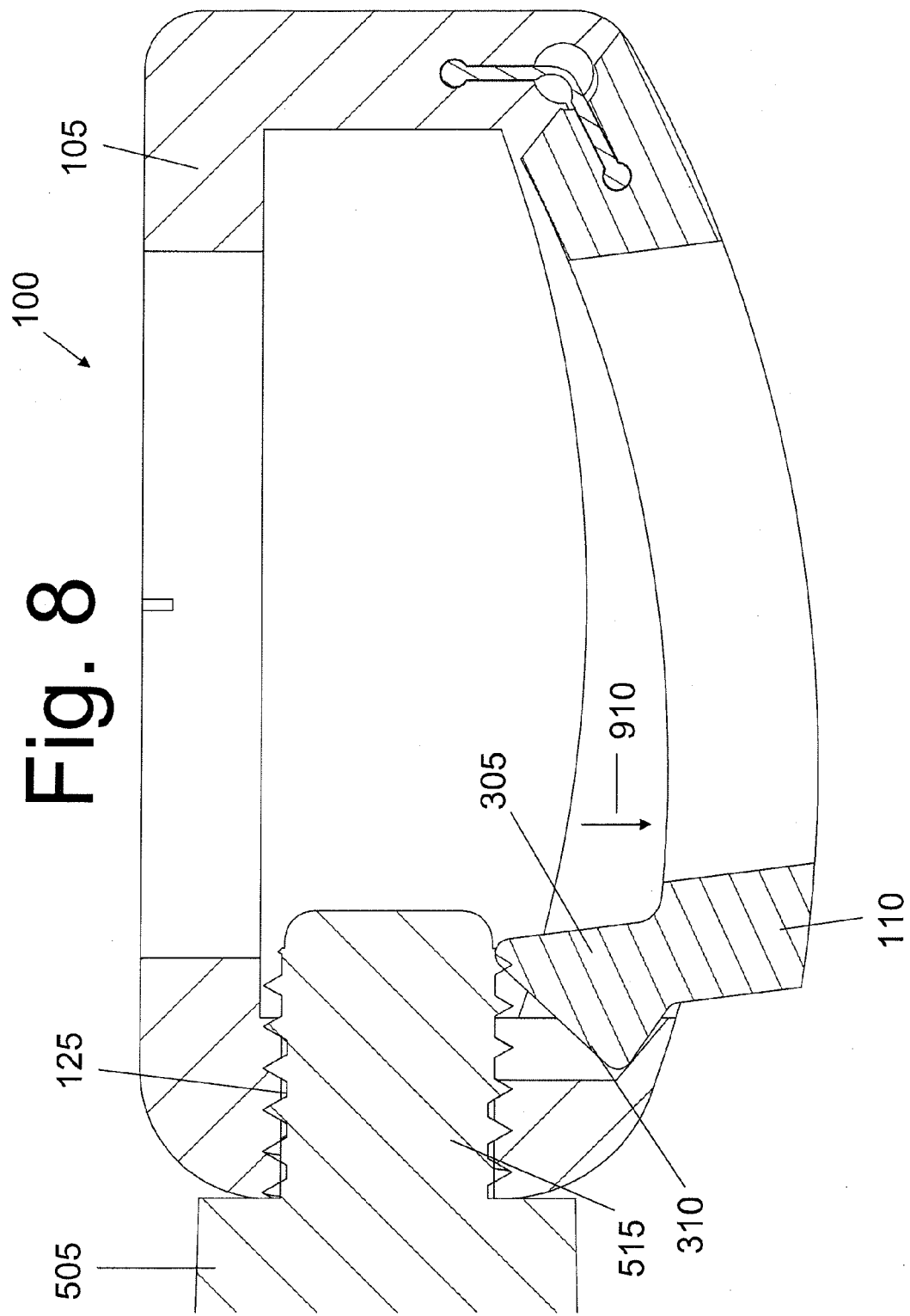
FIG. 8 shows cross-sectional, plan view of the cage with the insertion member coupled thereto.

The coupling of the insertion member 505 to the cage 100 and corresponding opening of the load member 110 is described in more detail with reference to FIG. 8. FIG. 8 shows cross-sectional, plan view of the cage 100 with the insertion member 505 coupled thereto. As the insertion member 505 is threaded into the borehole 125, the cage interface 515 abuts the abutment surface 310 of the projection 305 on the load member 505. The continued movement of the cage interface 515 further into the borehole 125 forces the load member outward (as exhibited by the arrow 910 in FIG. 9) with respect to the main body 105 and further away from the internal cavity defined by the main body 105.

The cage interface 515 can have a length such that an edge of the cage interface 515 protrudes at least partially into the internal cavity of the main body 105. In this manner, the protruding edge of the cage interface 515 can exert a load on the bone graft that is contained within the internal cavity, as describe further below.

In use, the insertion member 505 threaded into the main body 105 to cause the load member 110 to move into the open position such that it withdraws from the main body 105 of the cage. The insertion member 505 acts to hold the load member 110 in the open position. Using the insertion member 505 as a handle, an operator then implants the cage 100 in between a pair of vertebrae, such as between an upper vertebra and a lower vertebra. During implantation, an instrument can be advanced into the internal cavity to compact, compress and load the bone graft.

The internal cavity of the main body 105 is then packed with bone graft. The cavity can be packed with a sufficient volume of bone graft such that the bone graft fills the internal cavity.

Figure 9:
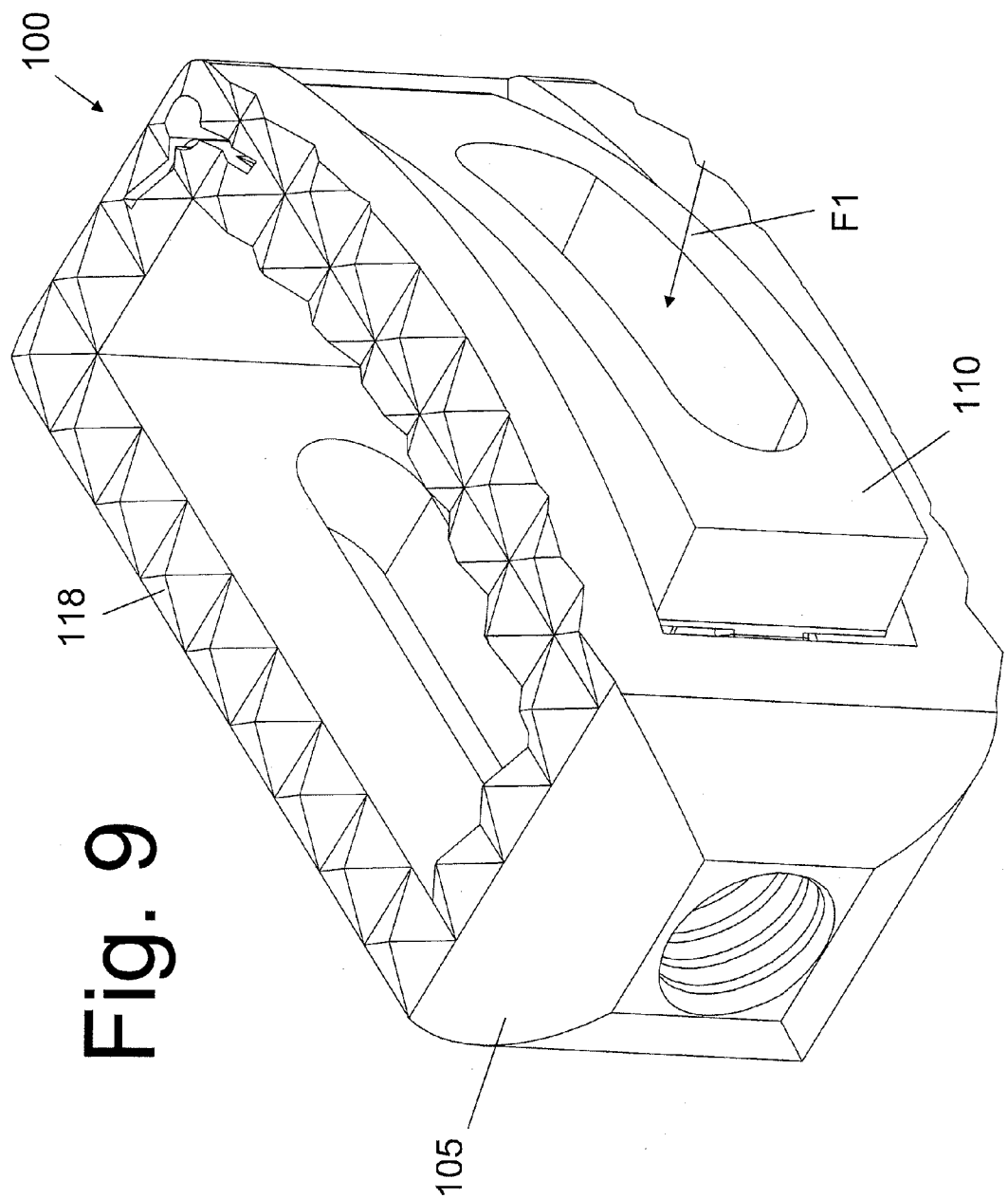
FIG. 9 shows the cage with the load member in the open position and the insertion member detached.

When positioned between the upper and lower vertebrae, the upper surface 118 of the main body 105 abuts or otherwise contacts the upper vertebra. The lower surface 120 abuts or otherwise contacts the lower vertebra. With the cage 100 positioned between the vertebrae, the insertion member 505 is detached from the cage 100. FIG. 9 shows the cage 100 with the load member 110 in the open position and the insertion member detached. For clarity of illustration, the upper vertebra and lower vertebra are not shown. The bone graft contained within the cage 100 is also not shown for clarity of illustration.

With the cage 100 implanted between the vertebrae, the main body 105 of the cage 100 provides structural support for the skeletal segment in which the upper and lower vertebra are positioned. That is, the cage 100 is of sufficient rigidity to bear structural loads that are transmitted through the vertebra. The main body 105 of the cage 110 has sufficient rigidity to shield such structural loads from the bone graft contained within the main body 105.

Although the main body 105 of the cage 100 shields the contained bone graft from the structural loads, the load member 110 provides a secondary load to the bone graft contained within the cage 100. When the insertion member 505 is detached from the cage 100, the cage interface 515 (shown in FIG. 9) no longer retains the load member 110 in the open position. As mentioned, the hinge 115 biases the load member 110 toward the closed position. Thus, the load member 110 is forced toward the internal cavity such that the load member 110 exerts a secondary load F1 (shown in FIG. 9) onto the bone graft contained within the main body 105. As mentioned, secondary load promotes fusion between the bone graft and adjacent bone of the skeletal system.

The bone graft within the cage 100 are pushed inwards in a horizontal plane and towards the upper and lower ends of the cage 100 in a longitudinal plane. The longitudinal component of the force increase the extent of contact between the bone graft and the vertebral surfaces whereas both components apply a constant force onto the graft. Both of these factors act synergistically to maximize the likelihood of bony fusion and optimize the quality of the fusion mass.

The cage 100 can include holes that extend through the upper and lower ends of the main body 105. When the load member 110 exerts the load against the bone graft contained within the main body, the bone graft can be urged to move upward and/or downward through the upper and lower holes. The force can urge the bone graft upward and downward out of the holes toward the upper and lower vertebra. In this manner, the bone graft is urged into increased surface contact with the neighboring bones. This promotes fusion between the bone graft and the neighboring bones.

Figure 10:
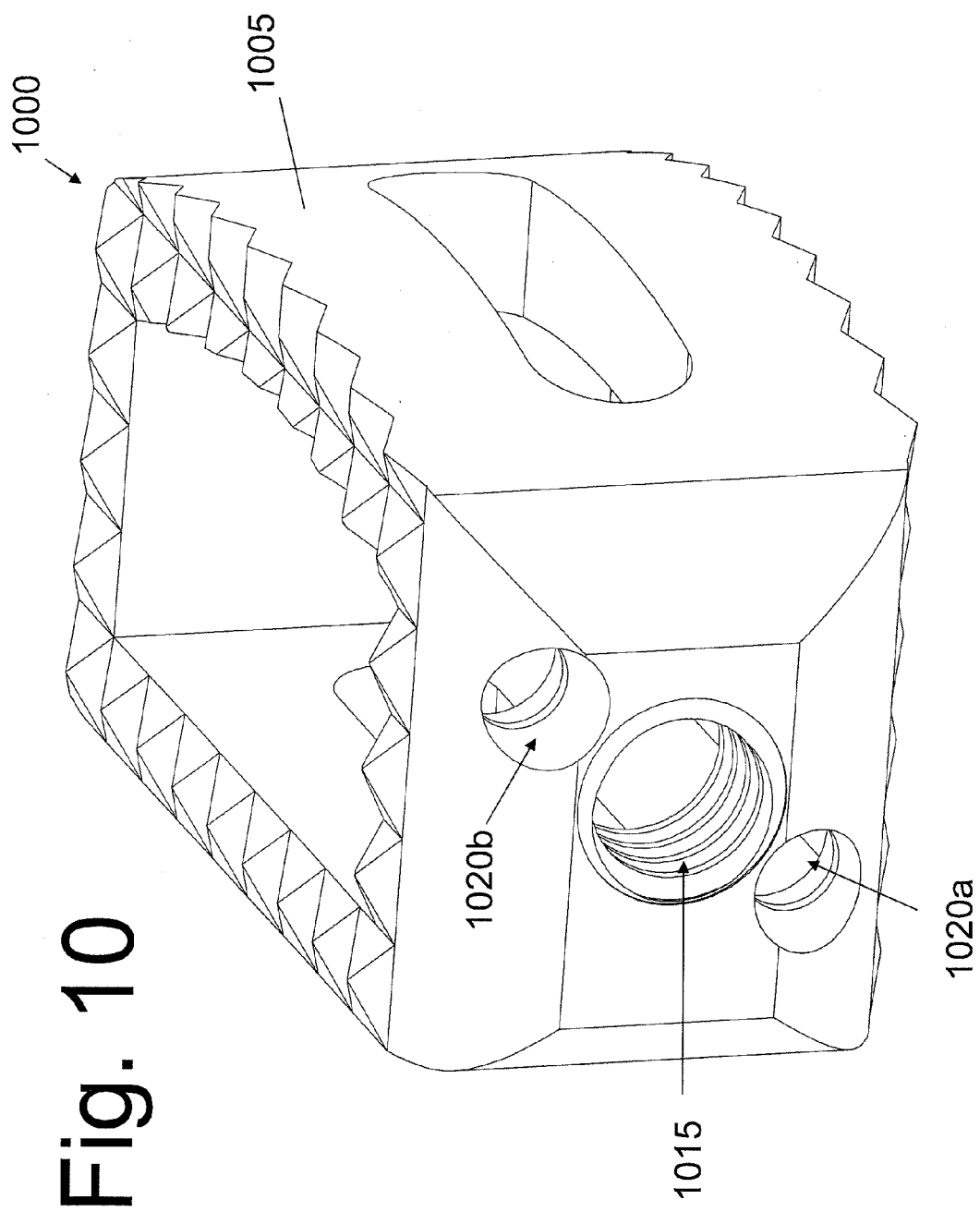
FIG. 10 shows another embodiment of a cage.

FIG. 10 shows another embodiment of a cage, which is referred to as cage 1000. The cage 1000 comprises a rectangular body 1005 having boreholes that extend through a sidewall. The boreholes includes a coupler borehole 1015 that is configured to receive an insertion member, as described below. A pair of load member boreholes 1020a and 1020b are also located on the sidewall. The load member boreholes 1020a, 1020b mate with a pair of extensions 1012 on a load member 1010.

Figure 11:
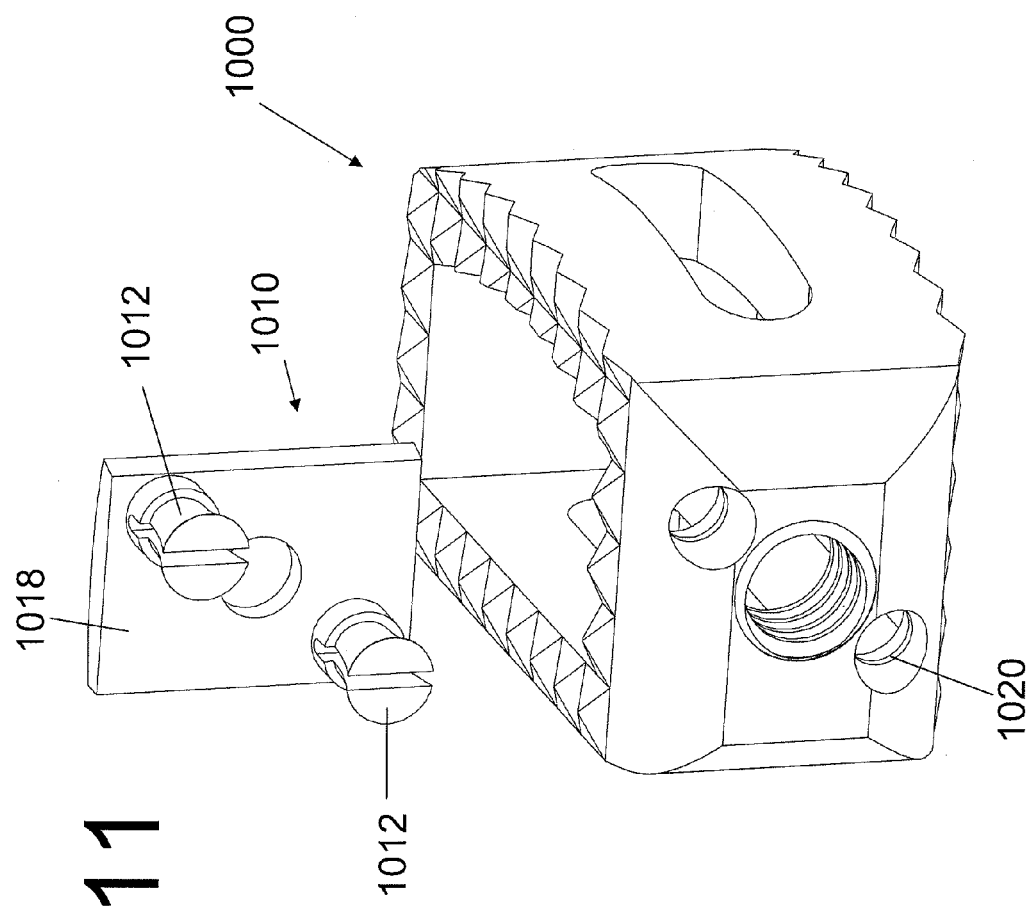
FIG. 11 shows a perspective view of the cage of FIG. 10 and a load member.
Figure 12:
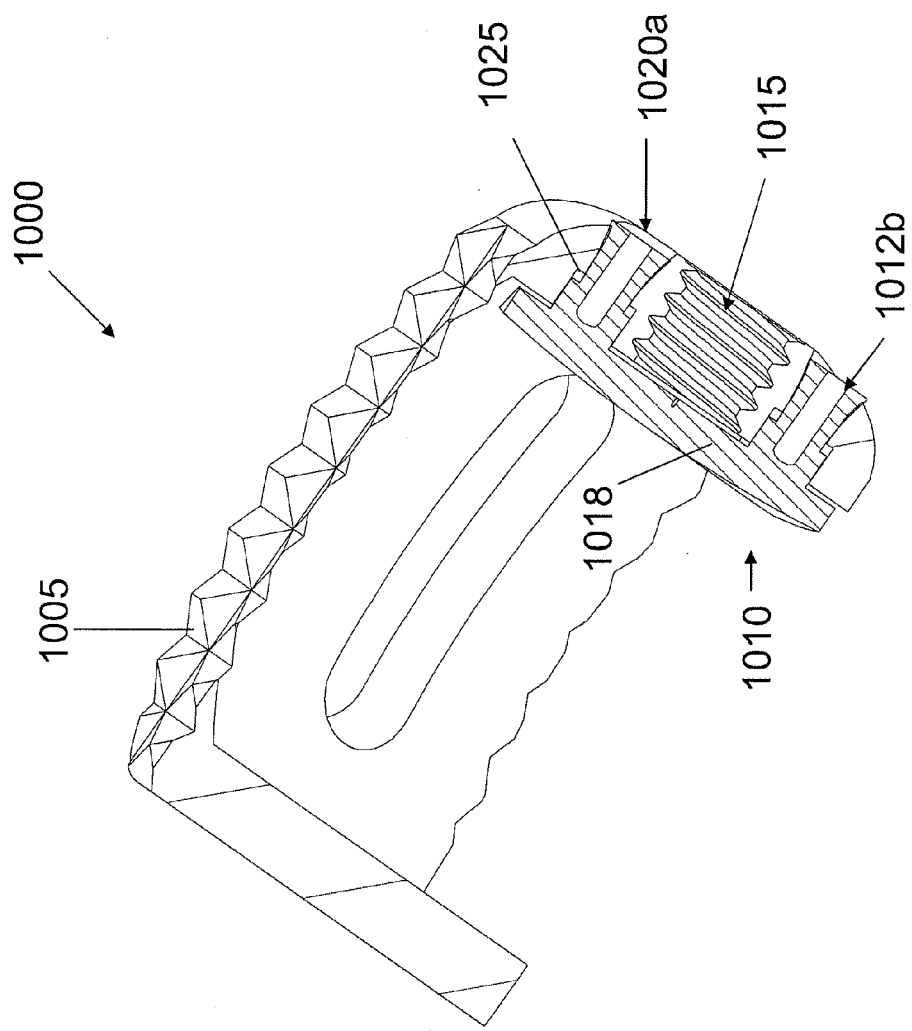
FIG. 12 shows a cross-sectional view of the cage of FIG. 10 with a load member in a withdrawn position.

The load member 1010 is shown in FIG. 11, which shows an exploded view of the cage 1000. The load member 1010 is a wall 1018 having a pair of extensions 1012 extending therefrom. The extensions 1012 are sized and positioned to fit within the load member boreholes 1020. FIG. 12 shows a cross-sectional view of the cage 1000 with the load member mounted in the load member boreholes 1020 with the load member in a withdrawn position. The extensions 1012 are frustoconical in shape and fit within the boreholes 1010 in a press-fit fashion. Each borehole 1020 includes a shoulder 1025 along its length.

Figure 13:
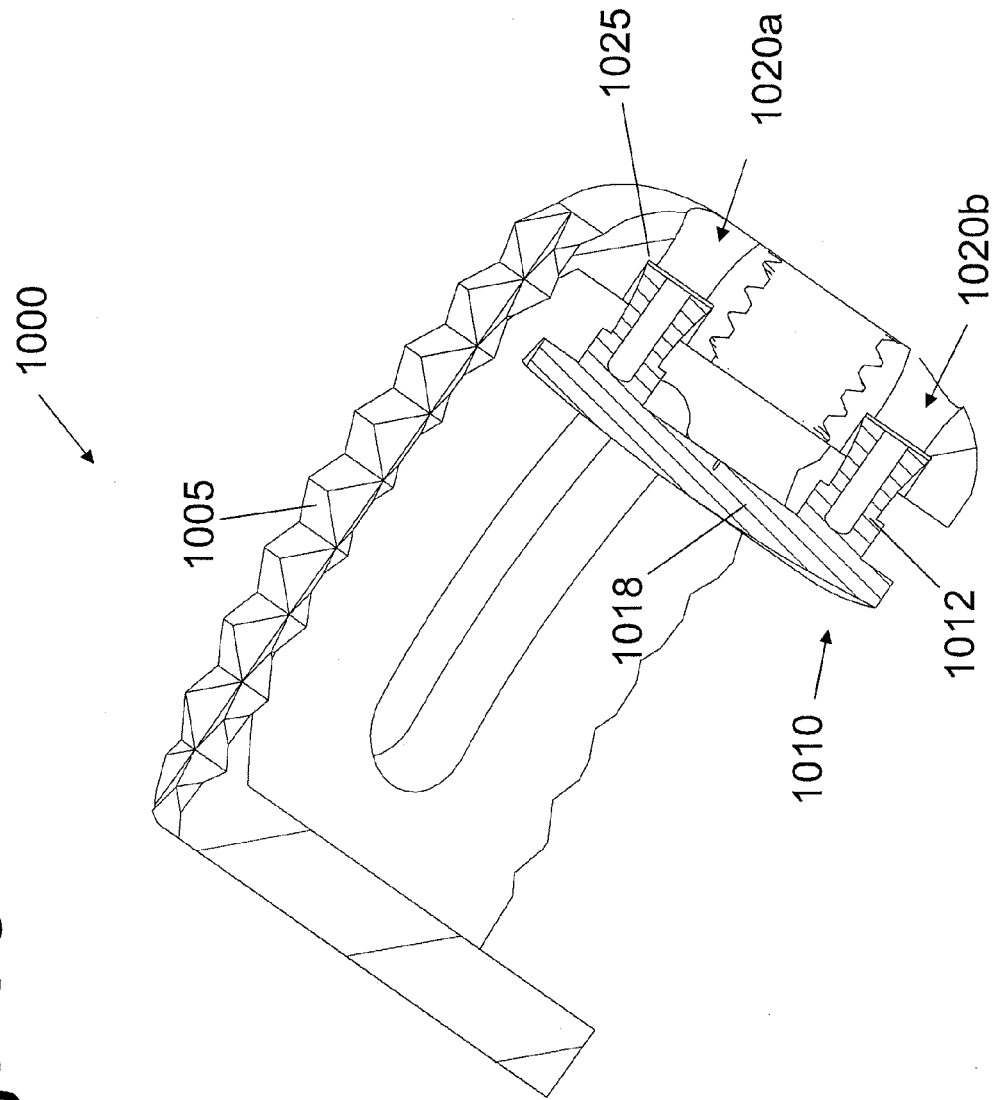
FIG. 13 shows a cross-sectional view of the cage of FIG. 10 with a load member in an extended position.

With reference to FIG. 13, the load member 1000 can be pushed into an extended position wherein the load member 1000 is positioned further inside the internal cavity of the cage 1000. The load member 1000 is moved inwardly relative to the body 1005 of the cage 1000 such that the extensions 1012 slide inwardly through the boreholes 1020. The extensions 1012 are configured to expand when they move past the shoulders 1025 such that the expand radially-outward once they move past the shoulders 1025. The edges of the extensions in combination with the shoulders 1025 thereby act as a detent to prevent the load member 1010 from sliding back in the outward direction through the boreholes 1020.

Figure 14:
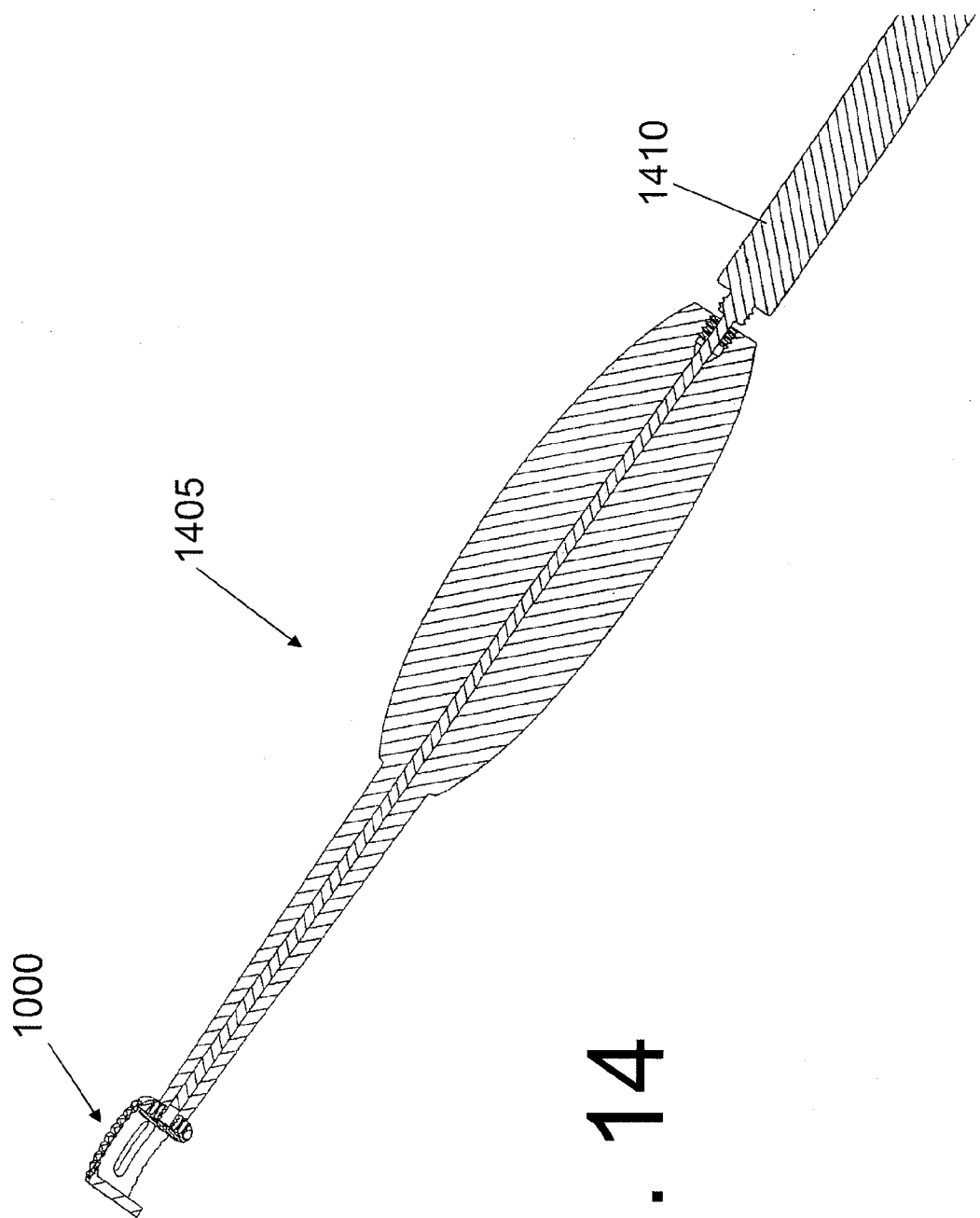
FIG. 14 shows a cross-sectional view of the cage coupled to an insertion member.

FIG. 14 shows a cross-sectional view of the cage 1000 coupled to an insertion member 1405. The insertion member includes an elongate rod having a handle at one end and a cage interface at an opposite end that removably mates with the borehole 1015 (shown in FIG. 10) of the cage 1000. The insertion member 1405 has an axial bore that is sized to receive a load member actuator 1410 that can be used to move the load member 1010 from the withdrawn position to the extended position. The load member actuator 1410 is an elongate rod having a length sufficient to be inserted entirely through the insertion member 1405.

Figure 15:
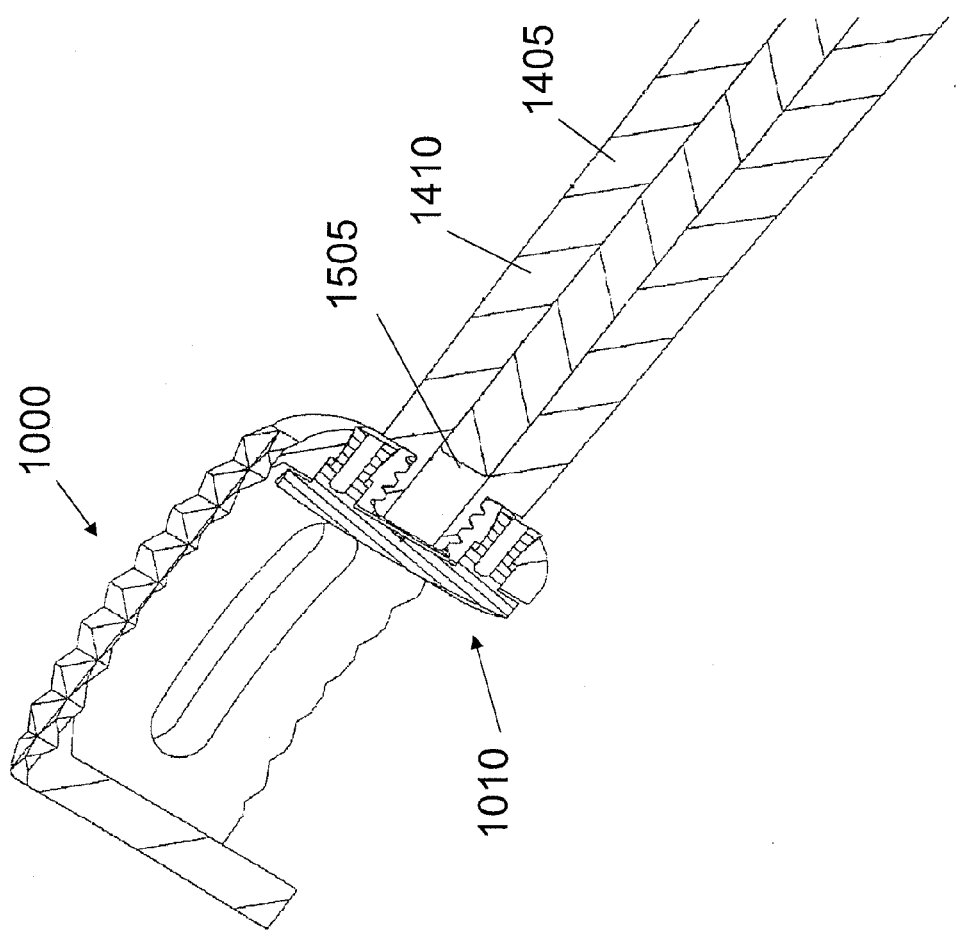
FIG. 15 shows an enlarged view of the cage with the load member in the withdrawn position and with the cage coupled to an insertion member.
Figure 16:
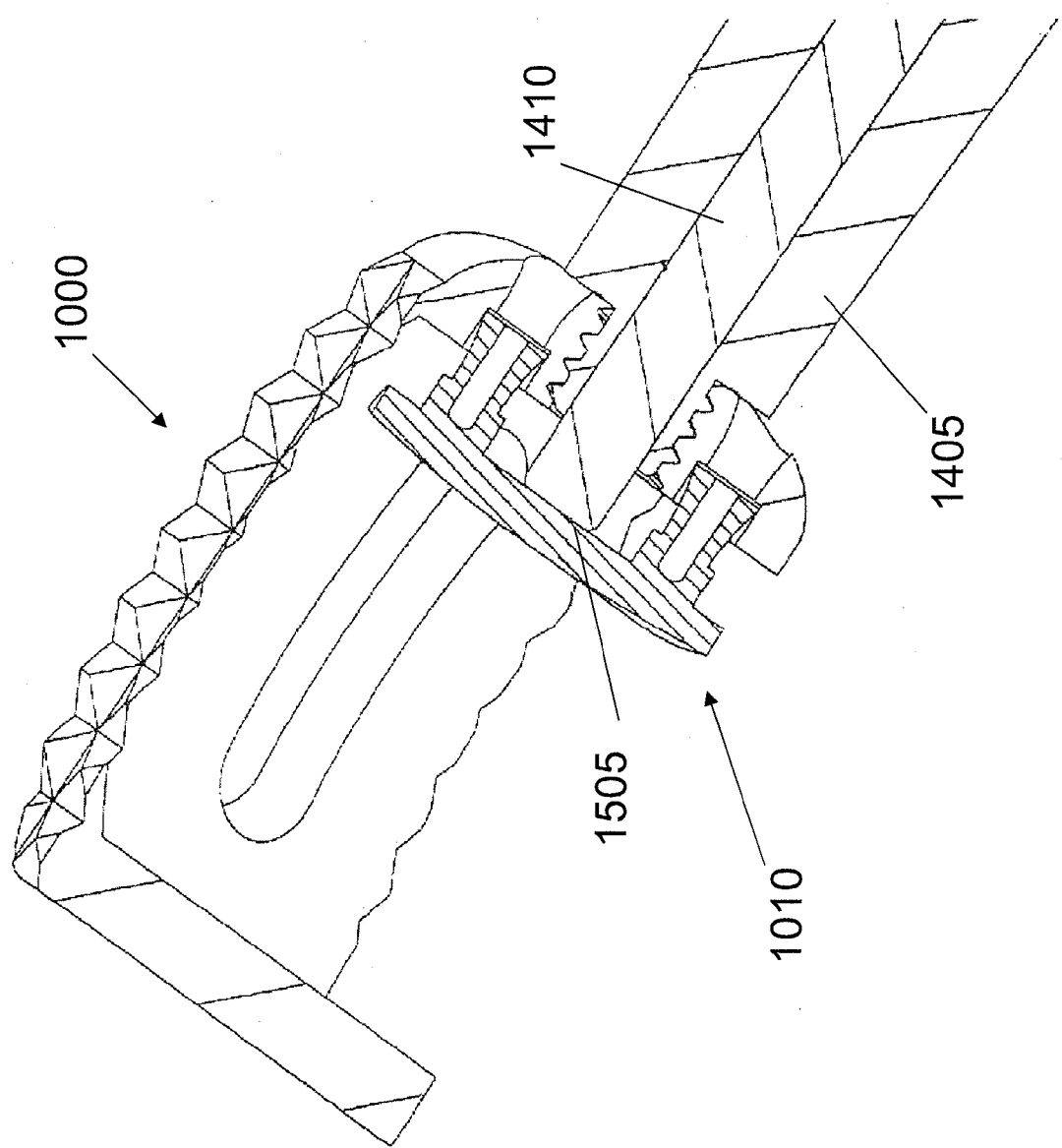
FIG. 16 shows an enlarged view of the cage with the load member in the extended position and with the cage coupled to an insertion member.

The manner in which the load member actuator 1410 moves the load member 1010 from the withdrawn position to the extended position is now described with reference to FIGS. 15 and 16. FIG. 15 shows an enlarged view of the cage 1000 with the load member in the withdrawn position and with the cage coupled to the insertion member 14015. The load member actuator 1410 is located within the insertion member 1405 with a distal end 1505 of the actuator 1410 spaced from the load member 1010.

To move the load member 1010 to the extended position, the load member actuator 1410 is pushed toward the load member 1010 such that the distal end 1505 of the actuator 1410 abuts the load member 1010. The load member actuator 1410 pushes the load member 1010 into the extended position, as shown in FIG. 16.

In use, the cage 1000 is positioned between a pair of vertebrae using the insertion member 1405, such as in the manner described above with respect to the previous embodiment. The cage 100 is then packed with bone graft while the load member is in the withdrawn position, as shown in FIG. 15. The load member actuator 1410 is then used to move the load member 1010 to the extended position. As the load member 1010 moves into the extended position, it exerts a load onto the bone graft contained within the cage. Advantageously, the main body 1005 of the cage 1000 supports structural loads of the skeletal system while the load member 1010 exerts a secondary load on the bone graft contained within the cage.

Figure 17:
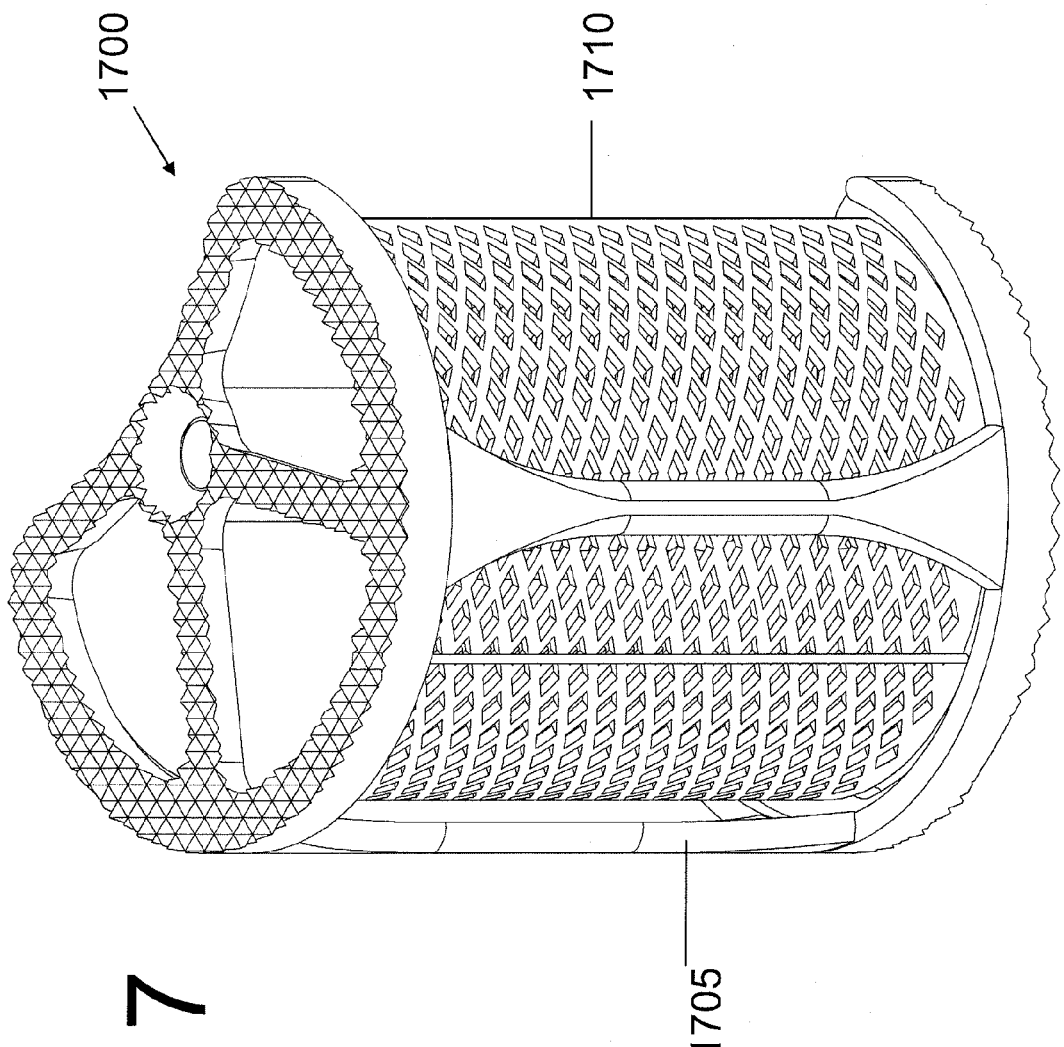
FIG. 17 shows yet another embodiment of a fusion cage.

FIG. 17 shows yet another embodiment of a fusion cage, referred to as cage 1700, which includes a rigid structural core 1705 and a load member comprised of a mesh screen 1708 that is coupled to the core 1705.

Figures 18A, 18B:
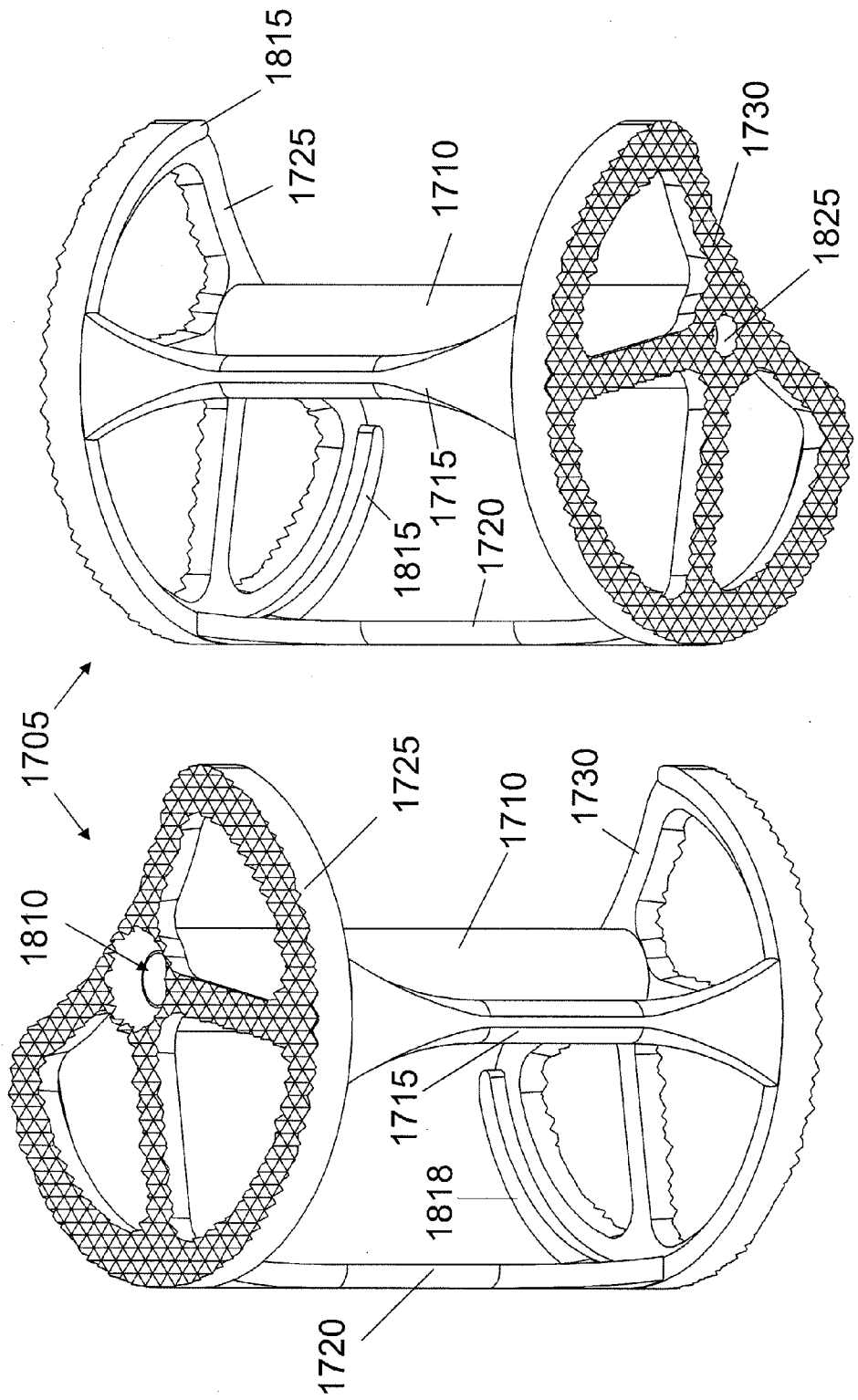
FIGS. 18A and 18B show perspective views of a structural core of the cage of FIG. 17.

FIGS. 18A and 18B shows upper and lower perspective view of the core 1705. The core 1705 includes three elongate struts including a main strut 1710 and a pair of secondary struts 1715, and 1720. The struts 1710, 1715,1720 support a pair of end segments, including an upper segment 1725 and a lower segment 1730. The strut 1710 has an internal axial bore with internal walls that can include threads.

With reference still to FIGS. 18A and 18B, the upper segment 1725 can be shaped like the vertebral end plate it is designed to rest against. The upper segment has one or more radially-extending portions that connect to a peripheral portion so as to form one or more holes through the upper segment 1725. In an exemplary embodiment, the segment 1725 includes a full thickness bore 1810 with a tapered opening, wherein the bore 1810 overlies the upper end the strut 1710 in the assembled device. The upper segment 1725 can include indentations (such as pyramidal indentations) on an upper surface, wherein the indentations rest against the lower surface of the upper vertebra.

FIG. 18B shows the underside of the upper segment 1725. A lip 1815 extends downwardly along the periphery of the upper segment 1725. The lip 1815 accommodates the mesh screen 1708 (shown in FIG. 17) of the cage 1700, as described below.

With reference to FIGS. 18A and 18B, the lower segment 1730 can also be shaped like the vertebral end plate it is designed to rest against. The lower segment 1730 has one or more radially-extending portions that connect to a peripheral portion so as to form one or more holes through the lower segment 1730. A full thickness bore 1825 (shown in FIG. 18B) without a tapered opening overlies the lower end of the strut 1710. The lower segment 1730 can include indentations (such as pyramidal indentations) on a lower surface, wherein the indentations rest against the upper surface of the lower vertebra.

FIG. 18A shows the upper side of the lower segment 1730. A lip 1818 extends upwardly along the periphery of the lower segment 1730. The lip 1818 accommodates the mesh screen 1708 (shown in FIG. 17) of the cage 1700, as described below.

The indentations on the upper and lower segments can be similarly-shaped but staggered. The staggered configuration permits two cages 1700 (an upper cage and lower cage) to staked on top of one another such that the pyramidal indentations of the lower end segment of the upper cage compliment the upper end segment of the lower cage. While the individual segments have been separately described, the cage 1700 can be a unitary device that is manufactured as one piece.

Figure 19:
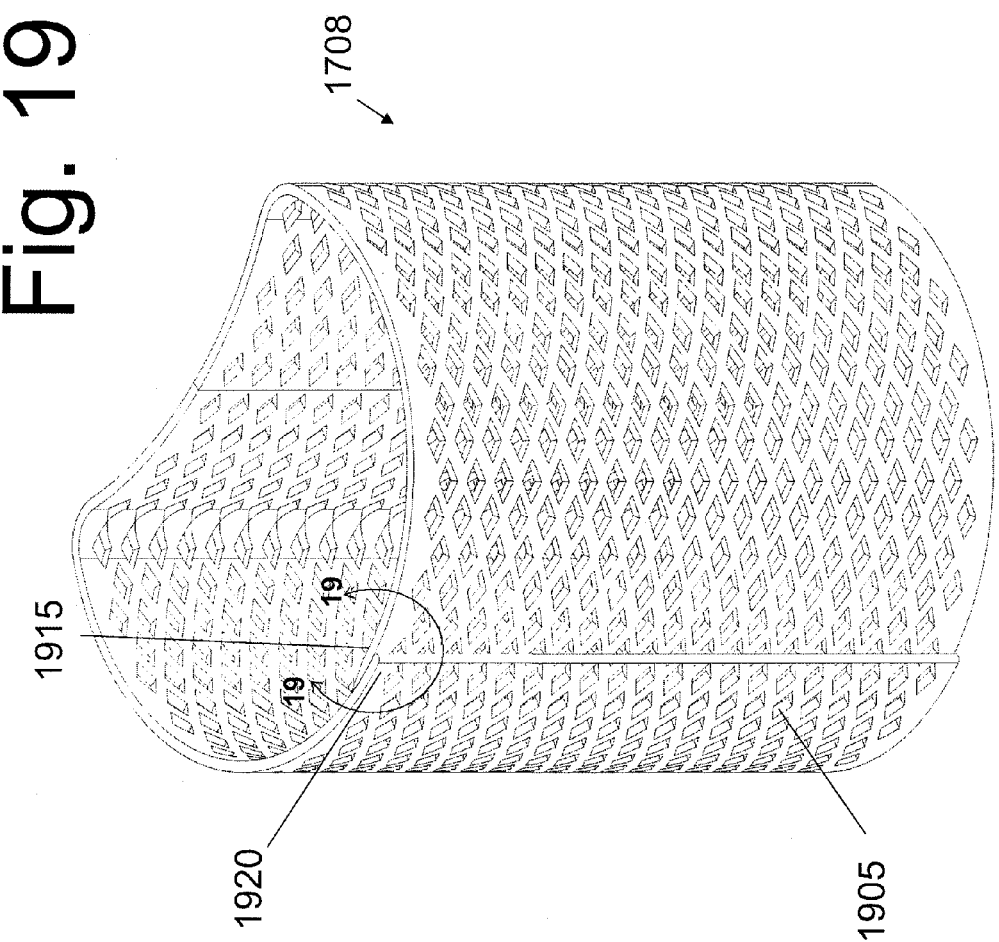
FIG. 19 shows the mesh screen of the cage of FIG. 17.

FIG. 19 shows the mesh screen 1708 of the cage 1700. The screen 1708 couples to the core 1705 to define an interior cavity that can contain bone graft. The screen 1708 defines an outer peripheral shape that substantially corresponds to the outer periphery of the segments 1725 and 1730. The screen 1708 defines a plurality of full thickness openings 1905, which may be of any geometric shape and occupy the total surface area of the screen 1708 or only a part of the screen 1708. In an alternate embodiment, the Screen 1708 is solid.

Figure 20:
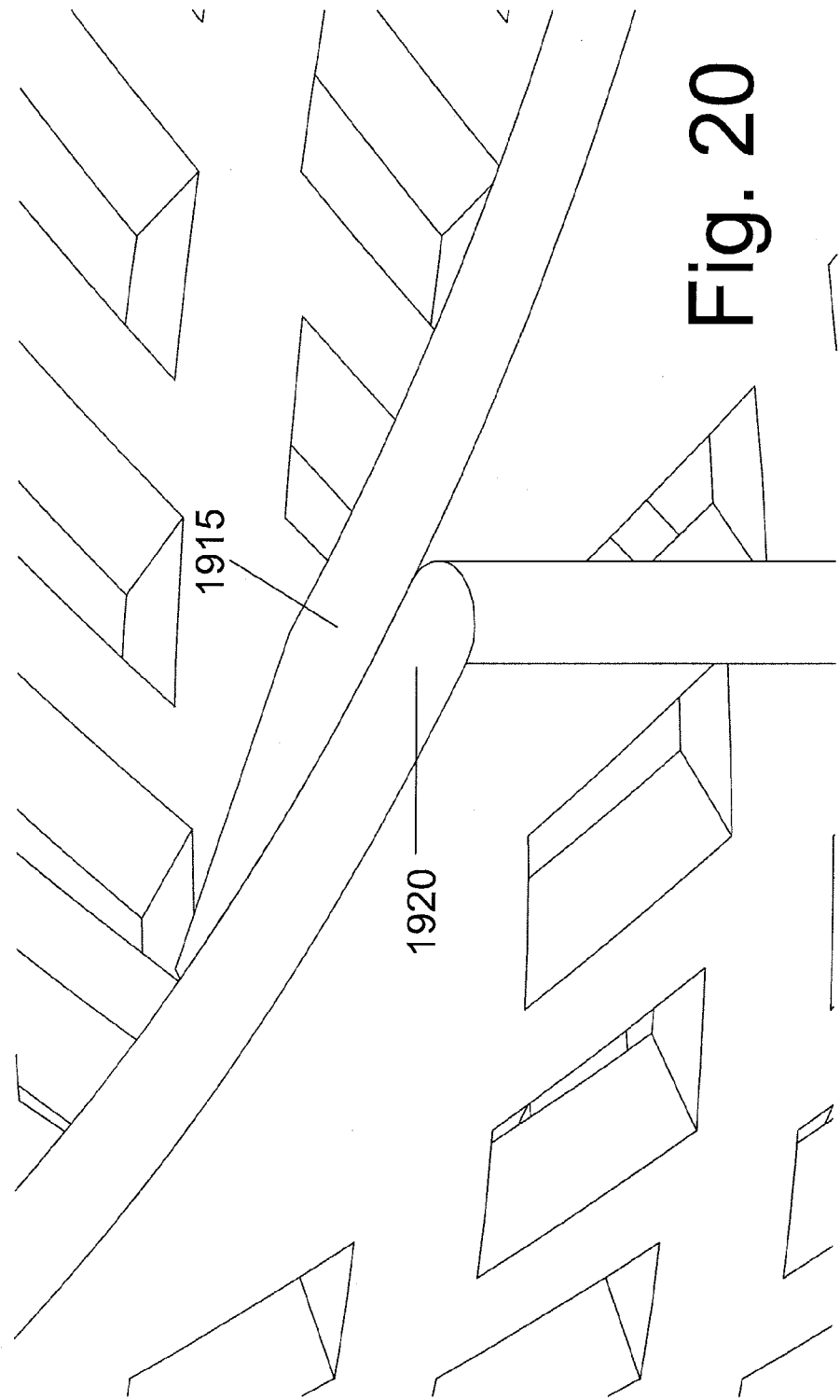
FIG. 20 shows an enlarged view of the portion of the screen contained within line 19-19 of FIG. 19.

The screen 1708 is a planar piece of material that is wrapped around itself in an annular fashion. The screen 1708 has a pair of edges 1915 and 1920 that overlap one another and that can be drawn apart from one another so as to permit a predefined amount of expansion when the interior cavity is packed with bone graft. FIG. 20 shows an enlarged view of the portion of the screen 1708 contained within line 19-19 of FIG. 19. As mentioned, the edges 1915 and 1920 overlap with one another. In one embodiment, the edge 1915 has a tapered thickness.

Any of the cages described herein or any of their components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. It would be understood by one of ordinary skill in the art that any system component can be made of any materials acceptable for biological implantation and capable of withstanding the load encountered during use. Any components may be further coated/made with osteo-conductive (such as deminerized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bioactive materials that promote bone formation.

Further, any instrument or device used in implant placement may be made from any non-toxic material capable of withstanding the load encountered during use. Materials used in these instruments need not be limited to those acceptable for implantation, since these devices function to deliver the implantable segments but are not, in themselves, implanted.

Figure 21:
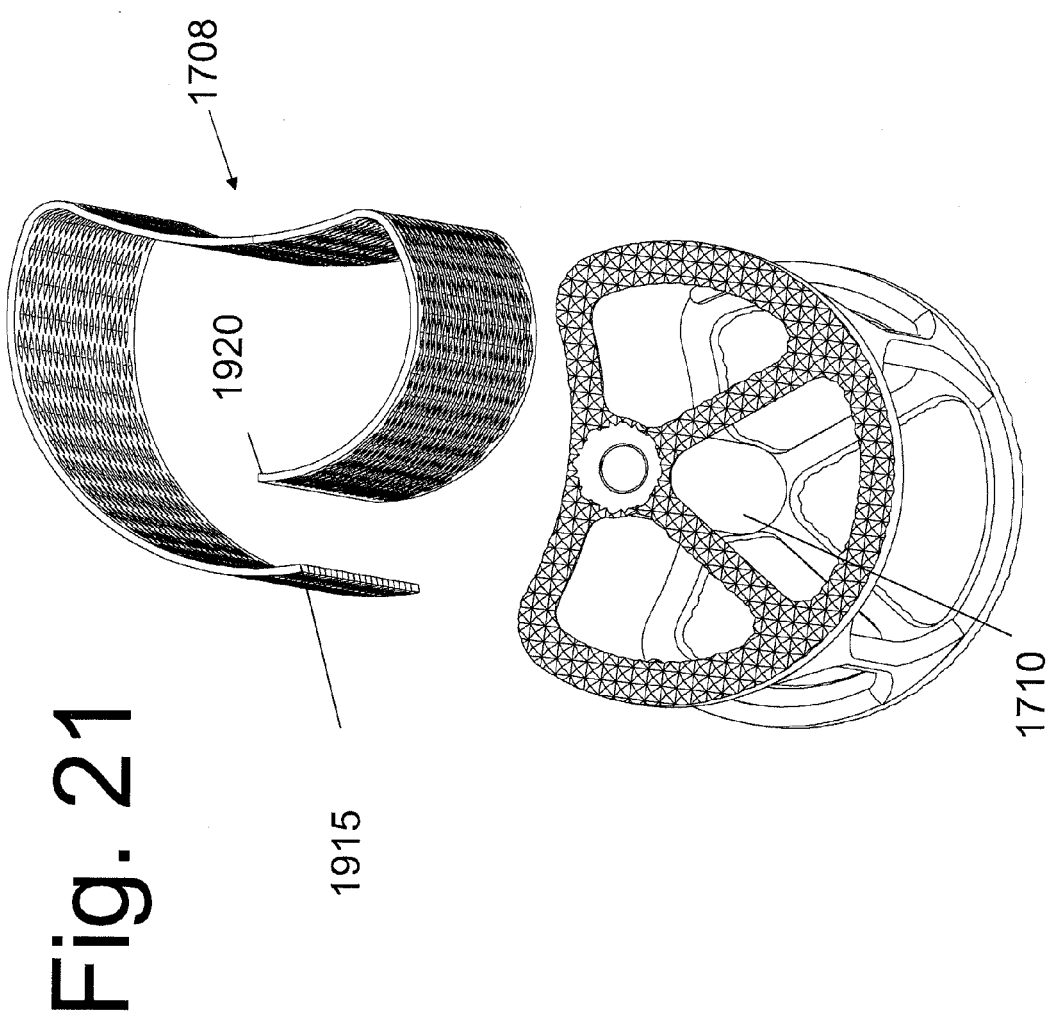
FIG. 21 shows the components of the cage of FIG. 17 prior to assembly.

FIG. 21 shows the components of the cage 1700 prior to assembly. During assembly of the device, the edges 1915 and 1920 of the screen 1708 are pulled apart from one another a distance sufficient to clear strut 1710. The screen 1708 is then inserted over and around the strut 1710 and then rotated into position. The screen 1708 is bounded on an outer surface by the upwardly and downwardly extending lips 1818 and 1815 (shown in FIGS. 18A and 18B) on the lower and upper segments. When in place, the screen 1708 can be retained by attachment to back end of the strut 11710 using any applicable technique that is acceptable for joining segments of those particular materials used for manufacture.

Figure 22A:
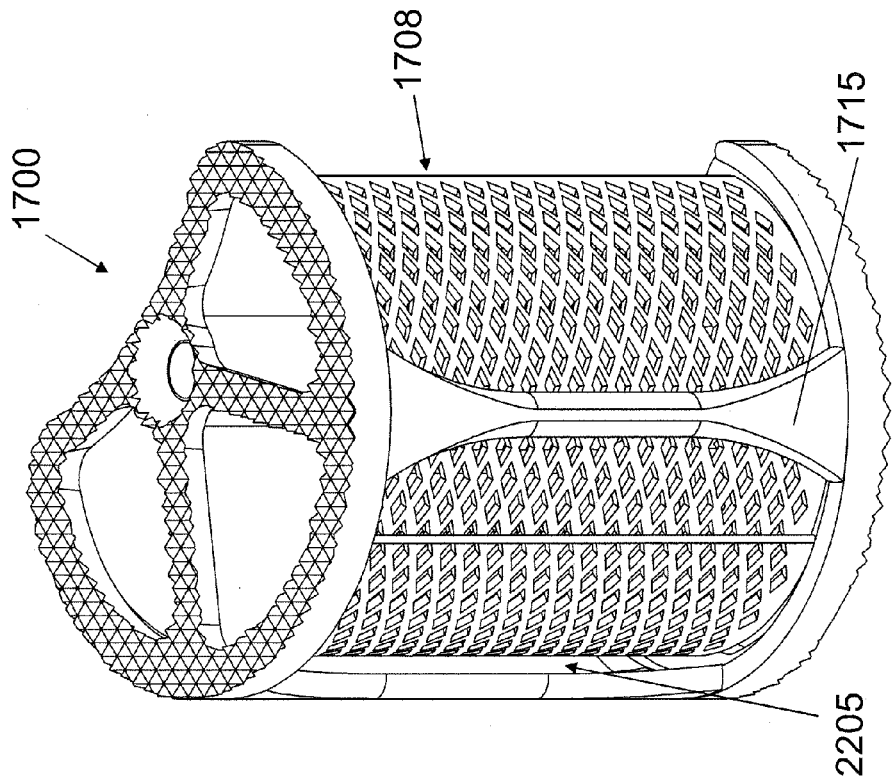
FIG. 22A shows the cage with the interior cavity empty such that the screen is in a relaxed position.
Figure 22B:
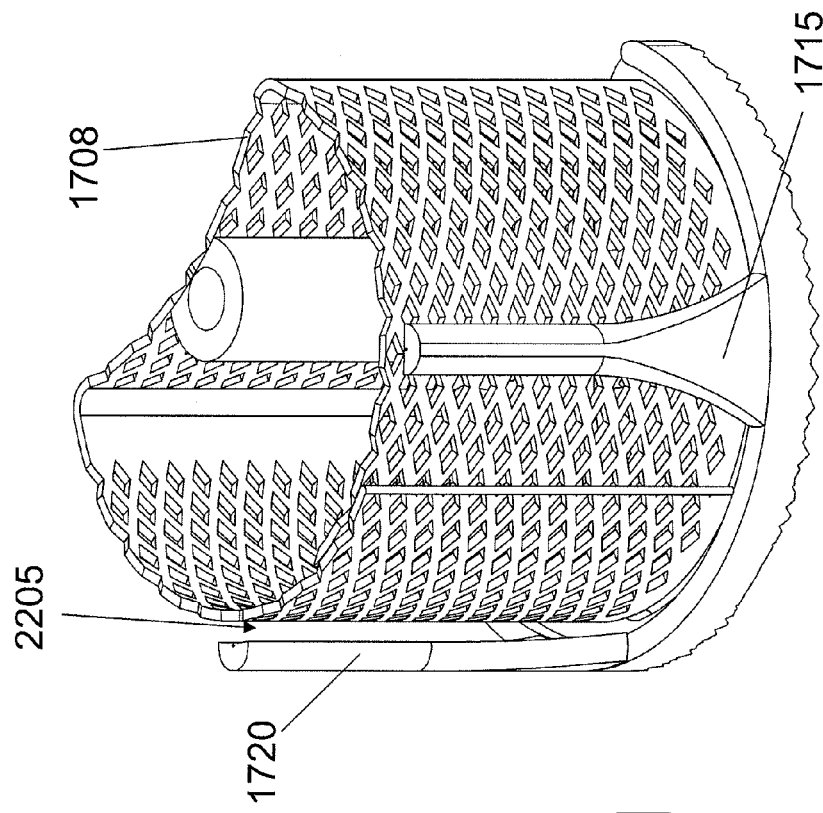
FIG. 22B shows a cross-sectional view of the cage with the interior cavity empty such that the screen is in a relaxed position.

FIG. 22A shows the cage 1700 with the interior cavity empty such that the screen 1708 is in a relaxed position. FIG. 22B shows a cross-sectional view of the cage 1700 with the interior cavity empty such that the screen 1708 is in a relaxed position. When the cage 1700 is empty and the screen 1708 in the relaxed position, a space 2205 exists between the struts 1715, 1720 and the outer surface of the screen 1708. The space 2205 is for outward expansion of the screen 1708 when the interior cavity is filled with bone graft.

Figure 23A:
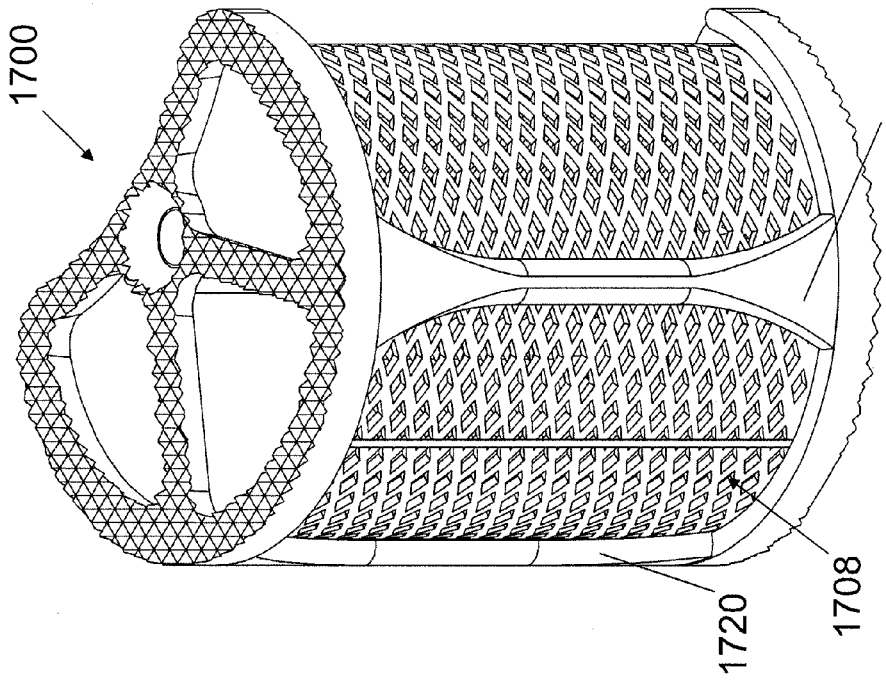
FIG. 23A shows the cage with the interior cavity packed with bone graft.
Figure 23B:
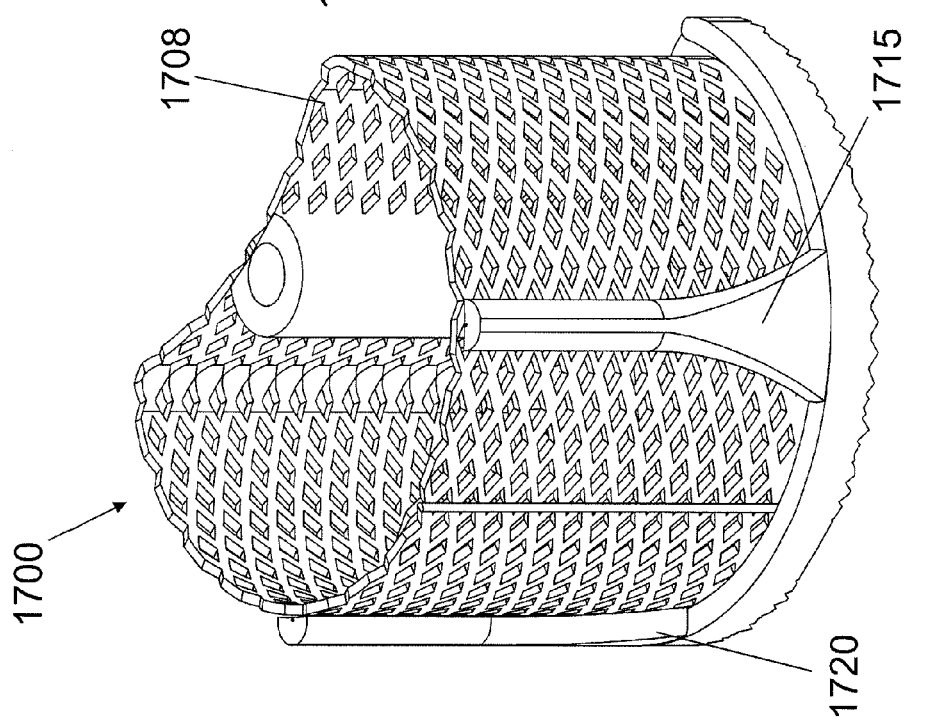
FIG. 23B shows a cross-sectional view of the cage with the interior cavity packed with bone graft.

The interior cavity can be packed with bone graft sufficient to cause the screen 1708 to expand outwardly over the space 2205. FIG. 23A shows the cage 1700 with the interior cavity packed with bone graft. FIG. 23B shows a cross-sectional view of the cage 1700 with the interior cavity packed with bone graft. (For clarity of illustration, the bone graft is not shown in FIGS. 23A and 23B.) Note that the bone graft has caused the screen 1708 to expand outward against the struts 1715, 1720 such that the space 2205 (shown in FIGS. 22A, 22B) is no longer present. It should be appreciated that the screen 1708 is biased inwardly such that it exerts a radially-inward load against the bone graft contained in the interior cavity of the cage 1700.

In the embodiment shown in FIGS. 17-23, the upper and lower segments 1725 and 1730 have outer surfaces that are parallel. It should be appreciated that the surfaces of the segments 1725 and 1730 can be non-parallel or contoured so as to conform to, complement, or otherwise recreate the curvature of the spinal segment they are intended to reconstruct.

FIG. 24A shows a perspective view of a wedge segment 2410 that can be placed against the upper or lower segments so as to achieve an inclined surface. FIG. 24B shows a side, cross-sectional view of the wedge segment 2410. The wedge segment has a bottom surface that can engage the upper surface of the upper segment 1725. The wedge segment further includes an upper surface that is inclined. The segment includes upper holes 2420.

Pyramidal indentations or other type of alignment structures are positioned along the upper, oblique surface that is intended to rest against the lower surface of the upper vertebra. Pyramidal indentations are also located along the straight bottom surface and interact with and compliment the indentations on the upper surface of the upper segment 1725.

A full thickness bore 2425 with a tapered opening extends through the wedge segment 2410 and aligns with the bore 1810 (shown in FIG. 18A) on the upper segment 1725 when the wedge segment 2425 is positioned atop the upper segment 1725

FIG. 25A shows a side, cross-sectional view of the cage 1700 with the wedge segment 2410 attached. FIG. 25B shows a perspective, cross-sectional view of the cage 1700 with the wedge segment 2410 attached. An elongate screw 2505 extends through the axial bore in the strut 1710. The screw 2505 can include threads that mate with threads inside the axial bore in the strut 1710.

The screw 2505 functions to retain the wedge segment 2410 on top of the cage 1700. In this regard, the screw 2505 has an enlarged head 2510 that abuts the upper end of the wedge segment 2410 to retain the wedge segment 2410 in place. The head can include indentation, which is intended to receive an engageable driver. While depicted as a hexagonal indentation, it is understood that any engageable head design and complimentary driver may be used.

FIG. 26 shows a pair of cages 1700 positioned atop one another to form a device of greater total length. Since individual cages can be manufactured in any variety of lengths, the ability to combine more than one cage greatly expands the number of overall lengths available to the user. Because the pyramidal indentations are staggered relative to one another, they compliment and interlock with one another when two cages are stacked. A screw 2610 similar to the screw 2510 (but longer) is used to hold the stacked devices together.

While not illustrated, a wedge segment 2410 may be added to the top of the stacked cages so that the end segments of the total device are not parallel. Alternatively, the top surface of the upper device can be made at an inclined angle. The lower surface of the lower device can also made at an inclined angle. In this way, the total (stacked) device can be made with non-parallel upper and lower surfaces.

In use, a distraction instrument is used to grab the screen 1708 of an empty cage 1700. The openings 1905 (shown in FIG. 19) can be used to grab hold of the screen 1708. The instrument applies a distraction force across the open end of the screen 1708 thereby opening it. The distraction force is maintained while the interior cavity of the cage 1700 is packed with bone graft, such as through the openings in the upper or lower end segments.

The distraction instrument is used to hold and guide the packed cage 1700 into the operative site and properly position it, such as between an upper vertebra and a lower vertebra. At this stage, the radially-inward force exerted by the bias of the screen 1708 is countered by the distraction instrument such that the bone graft does not experience any compressive force from the screen 1708. However, the bone fragments are retained within the cage 1700 by the force used to pack them into the cage 1700.

Once the cage 1700 is properly positioned between the vertebra, the distraction instrument is released and the same instrument is used to compress the screen edges. In this way, a centripetal, compressive force is applied to the bone graft inside the cage 1700 and the force is maintained by the memory inherent in the material used to manufacture the screen 1708. The applied force will also drive the bone graft within the cage 1700 towards the upper and lower end and increase the contact between the caged bone and the vertebral bone.

FIG. 27 shows a perspective view of a cage 2700 that includes a cylindrical outer wall that defines an interior cavity. As shown in the cross-sectional view of FIG. 28, the interior cavity of the cage 2700 is enclosed at one end by a wall and open at an opposite end. Threads 2805 are located in the interior of the outer wall at the opening to the interior cavity.

Figure 29:
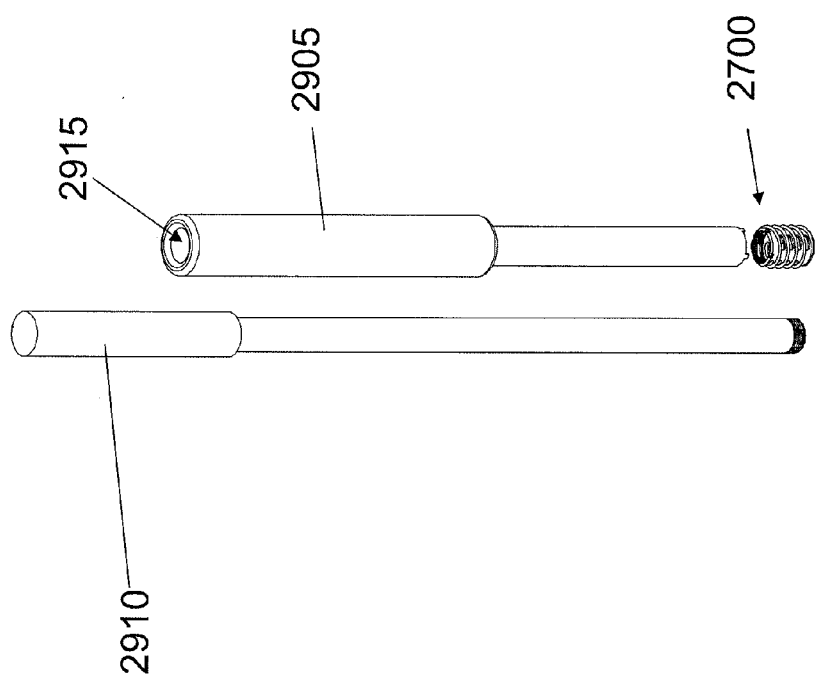
FIG. 29 shows a perspective view of the fusion cage and an insertion/load system for use with the cage.
Figure 30:
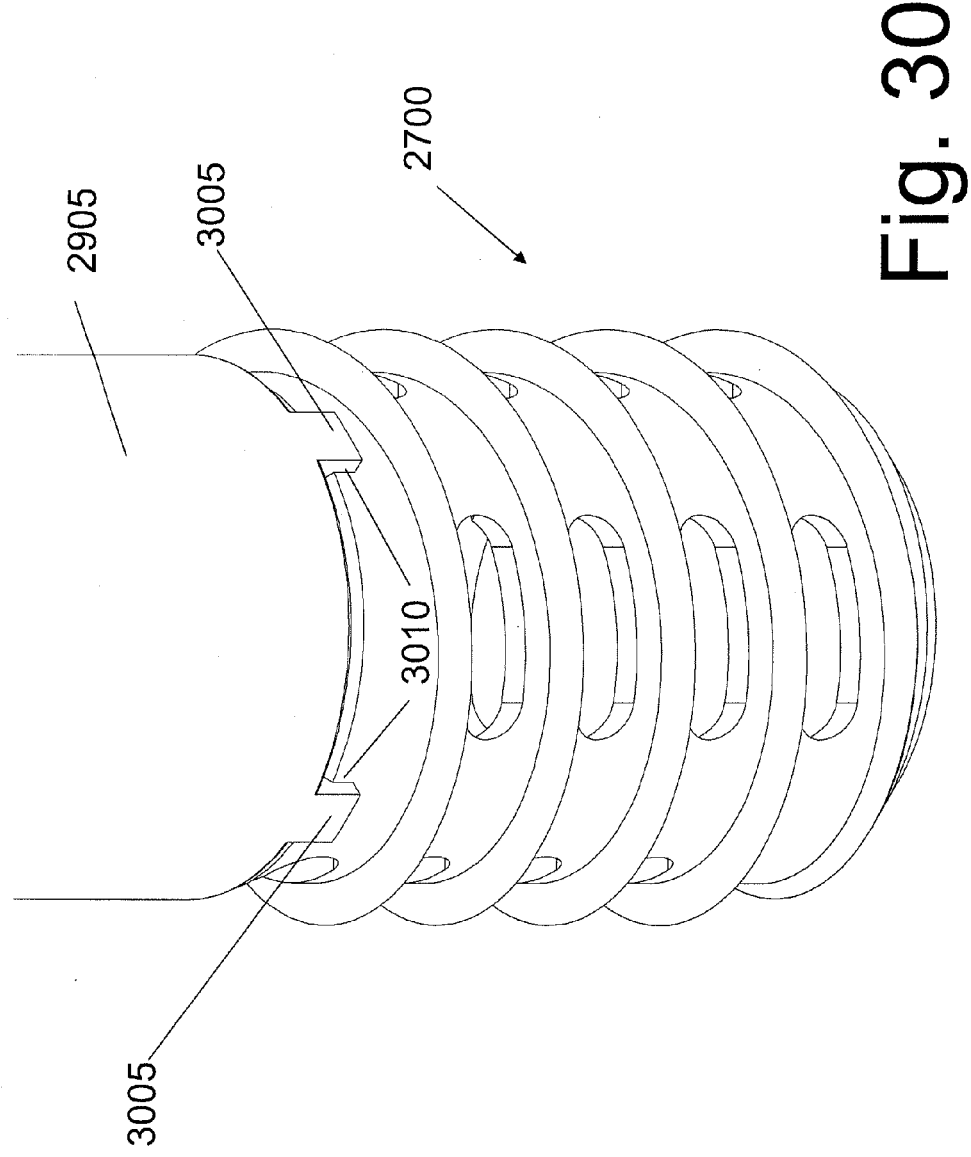
FIG. 30 shows an enlarged view of the cage coupled to the insertion/load system.

FIG. 29 shows a perspective view of an insertion member 2905 and a load member 2910 for use with the cage 2700. The insertion member 2905 is an elongate road having an internal shaft 2015 that receives the load member 2910. As shown in the enlarged view of FIG. 30, an end of the insertion member 2905 includes coupling members, such as tabs 3005 that mate with coupling members, such as complementary-shaped notches 3010 (shown in FIGS. 27 and 28), in the cage 2700. The tabs 3005 can be mated with the notches 3010 to removably couple the insertion member 2905 to the cage 2700.

Figure 31:
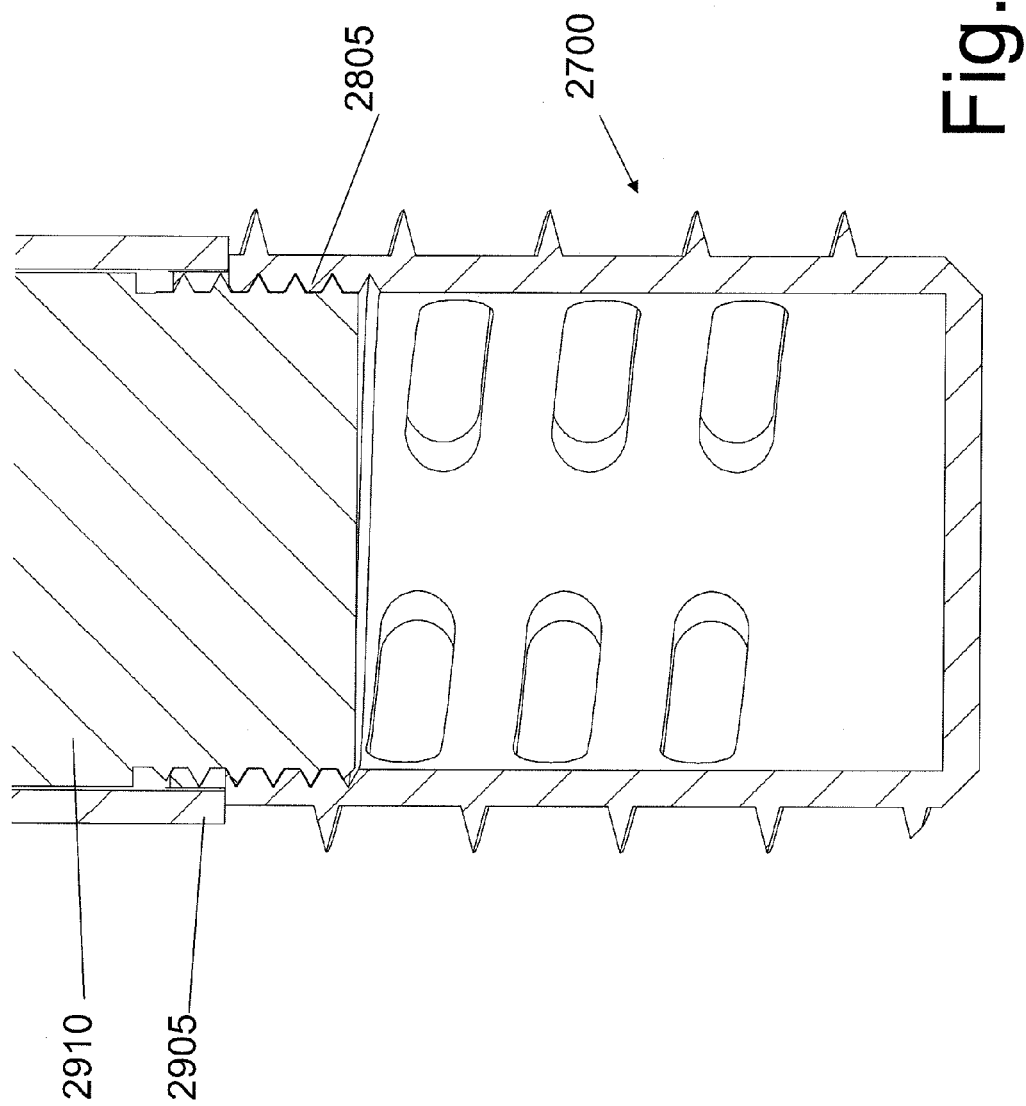
FIG. 31 shows an enlarged, cross-sectional view of the cage coupled to the insertion/load system.

The cage 2700 is packed with bone graft and implanted between a pair of bones using the insertion member 2905. When the insertion member 2905 is coupled to the cage 2700, the load member 2910 is inserted into the shaft 2015 such that the end of the load member 2910 protrudes out of the insertion member 2905 and into the internal cavity of the cage 2700, as shown in FIG. 31. The end of the load member 2910 has threads that mate with the threads inside the cage 2700. The load member 2910 is then threaded downwardly so that it protrudes further into the internal cavity of the cage 2700. The end of the load member 2910 can be used to exert a load onto bone graft that has been packed into the internal cavity of the cage 2700. In this manner, a secondary load can be exerted onto the graft during insertion of the cage between bones.

Figure 32:
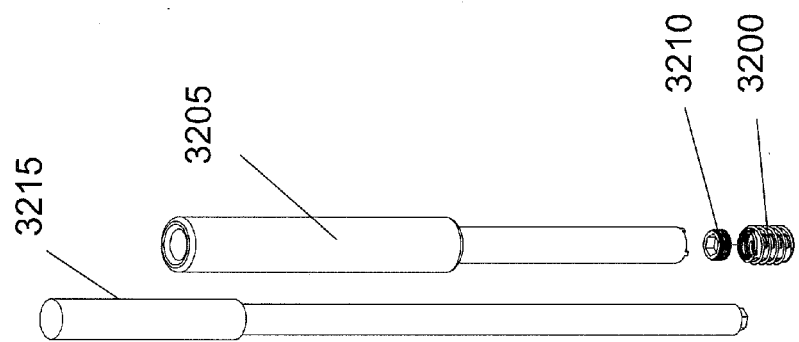
FIG. 32 shows another embodiment of a cage and a insertion/load system.

FIG. 32 shows yet another embodiment of a cage 3200 and an insertion/load system that includes an insertion member 3205 and a load member driver 3215. The cage 3200 is similar to the cage 2700 described above, although the cage 3200 includes a load member 3210 comprised of a nut that having external threads that mate with the threads in the opening of the cage 3200.

Figure 33:
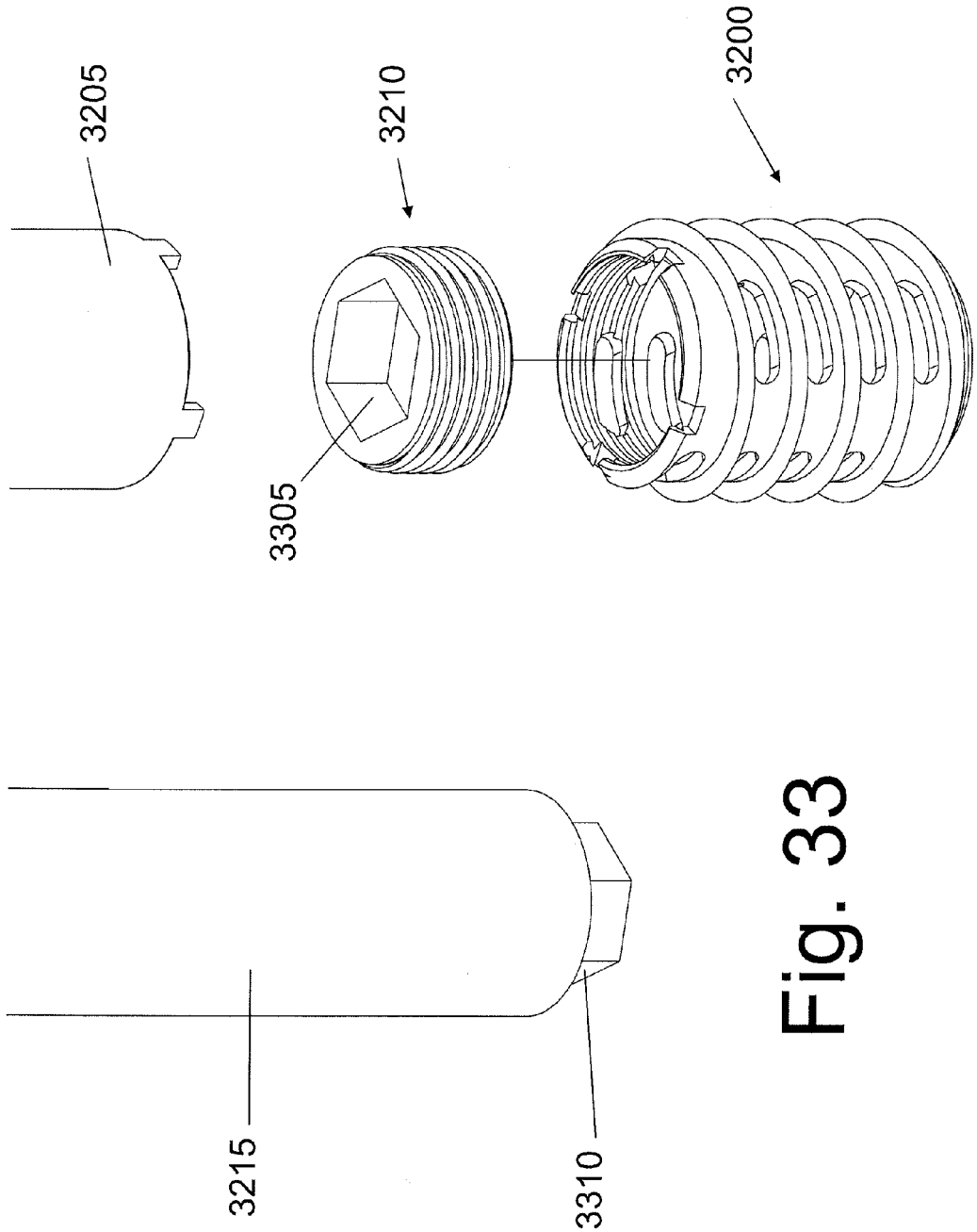
FIG. 33 shows an enlarged view of the cage member and the insertion/load system.

As shown in FIG. 33, the insertion member 3205 has coupling members (such as tabs) that mate with coupling members (such as notches) in the cage 3200. The load member 3210 has a cavity 3305 or other coupling means that mates with a driver 3310 (such as a hexagonal extension) on the end of the load member driver 3215.

FIG. 34 shows a cross-sectional view of the cage 3200 coupled to the insertion member 3205 and the load member driver 3215. The driver 3310 is inserted into the cavity 3305 in the load member 3210. The driver 3310 can be rotated to cause the load member 3210 to move further into the internal cavity in the cage 3200 such that the load member 3210 exerts a secondary load on bone graft contained within the cage 3200. That is, the load member 3210 compressed bone graft within the cavity. In an alternative embodiment, the load member 3210 is spring-loaded such that it is biased toward the internal cavity to exert a constant load onto bone graft contained within the internal cavity.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A fusion implant adapted to fuse bone within a skeletal system, comprising:
 a body sized and shaped for implanting between bones of a skeletal system, the body defining an internal cavity configured to contain implanted bone graft or bone graft substitute, wherein the body includes a first skeletal bone abutment surface and a second skeletal bone abutment surface both surfaces being adapted to abut adjacent skeletal bones, wherein the abutment surfaces are connected by at least one wall and wherein, when implanted. in the skeletal system, the skeletal bone abutment surfaces support a structural load transmitted through the skeletal bones when implanted in the skeletal system;
 a load member that forms at least a portion of the boundary of the internal cavity, wherein the load member that is separate from the wall of the body and does not form a portion of the abutment surface, and wherein the load member is spring biased to move towards the internal cavity and provide a compressive load upon the contained bone graft material.

2. An implant as in claim 1, wherein the body shields bone graft contained within the body from the structural loads.

3. An implant as in claim 1, wherein the body partially shields bone graft contained within the body from the structural loads.

4. An implant as in claim 1, wherein the load member comprises a door pivotably attached to the body, wherein the door is spring biased toward the internal cavity of the body such that the door exerts the compressive load onto the bone graft contained within the body and wherein the door fits within an opening located in a side wall of the body.

5. An implant as in claim 1, wherein at least one hole extends through a skeletal bone abutment surface of the body and wherein the compressive load provided by the load member forces at least a portion of bone graft contained within the internal cavity through the hole and toward a skeletal bone surface that abuts the implant Previously presented when the body is implanted.

6. An implant as in claim 1, further comprising an insertion member that detachably couples to the body, the insertion member comprising an elongate rod having a handle on one end and an interface on another end, the interface detachably coupling to the body.

7. An implant as in claim 1, wherein at least a portion of the load member has a height that is less than the distance between the top and bottom skeletal bone abutment surfaces of the implant when the height distance is measured at the site of the load member.

8. An implant as in claim 7, wherein at least one of the skeletal bone abutment surfaces contains a sill that is positioned between the load member and the skeletal bone surface.

9. A bone fusion implant, comprising:
 a device for implanting between bones of a skeletal system, the device containing at least one cavity for containing implanted bone graft or bone graft substitute so that the implanted bone graft or bone graft substitute can form a bone fusion mass with at least one adjacent skeletal bone, wherein the device is adapted to bear structural loads transmitted through the skeletal system, the device having a first skeletal bone abutment surface and a second skeletal bone abutment surface both surfaces being adapted to abut adjacent skeletal bones, wherein the abutment surfaces are connected by at least one wall; and
 a load member movably attached to the device, the load member adapted to exert a compressive load upon the implanted bone graft or bone graft substitute implanted within the internal cavity, wherein the load member is spring biased to move towards the internal cavity and compress the bone graft material contained within it, and wherein, at the location of the load member, the distance between the first and second skeletal bone abutment surfaces is greater than the height of the load member.

10. The system of claim 9, wherein the device shields bone graft contained within the body from the structural loads.

11. The system of claim 9, wherein the device partially shields bone graft contained within the body from the structural loads.

12. The system of claim 11, wherein the device transmits a portion of the structural loads to the bone graft contained within the device.

13. The implant of claim 9, wherein the load member includes a top surface and a bottom surface and wherein, at the location of the load member, the distance between the first and second skeletal bone abutment surfaces of the implant is greater than the distance between the top and bottom surfaces of the load member.

14. An implant as in claim 9, wherein at the location of the load member, the distance between the first and second bone abutment surfaces of the device is greater than the distance between the top and bottom surfaces of the load member.

15. A method of fusing a pair of bones in a skeletal system, comprising:
 providing an implant having a first skeletal bone abutment surface, a second skeletal bone abutment surface, at least one cavity that is configured to contain implanted bone graft or bone graft substitute, and a load member that at least partially defines the boundary of the cavity, wherein the load member can reversibly transition from a first state where the cavity has a first volume to a second state where the cavity has a second volume, wherein the first volume is greater than the second volume and wherein the load member is spring biased towards the second state;
 using an instrument to retain the load member of the implant within the first state;
 packing the cavity of the implant with bone graft or bone graft substitute, wherein the implant contains at least one opening that allows the contained bone graft or bone graft substitute to contact at least one surface of adjacent skeletal bone;
 placing the implant adjacent to skeleton bones such that the bone graft or bone graft substitute within the implant cavity is in contact with at least one adjacent skeletal bone;
 causing the load member to move towards the cavity that contains the bone graft material by releasing the instrument used to retain the load member in the first state.

16. A method as in claim 15, wherein the compression applied by the load member urges the bone graft or bone graft substitute to pass through the opening, toward the adjacent bone and into contact with the adjacent bone.

17. An implant as in claim 15, wherein, after the completion of the placing step, at least a portion of the load member remains movable relative to at least one skeletal bone surface that abut the implant.

18. A method of bone fusion in an animal or human subject, comprising:
 coupling an orthopedic device to a placement instrument, wherein the device includes a first abutment surface, a second abutment surface, at least one side member connecting the abutment surfaces, and an internal cavity at least partially defined by the abutment and side member and adapted to contain a bone forming substance, wherein the internal cavity communicates with the external aspect of the device through at least one opening and wherein the device further contains a load member, wherein the load member can reversibly transition from a first state where the cavity has a first volume to a second state where the cavity has a second volume, wherein the first volume is greater than the second volume and wherein the load member is spring biased towards the second state;

packing the internal cavity of the device with a bone forming substance, wherein the load member is in the first state at an onset of the packing procedure;

positioning the device adjacent to at least one bone surface and orienting the device so that the internal cavity communicates with at least one bone surfaces; and uncoupling the placement instrument from the orthopedic device and causing the load member to move towards the cavity that contains the bone forming substance and compress the material contained therein.

\* \* \* \* \*

UNITED STATES PATENT AND TRADEMARK OFFICE
CERTIFICATE OF CORRECTION

PATENT NO.       : 7,641,690 B2                                              Page 1 of 1
APPLICATION NO.  : 11/211160
DATED            : January 5, 2010
INVENTOR(S)      : M. Samy Abdou It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 375 days.

Signed and Sealed this

Sixteenth Day of November, 2010

David J. Kappos
*Director of the United States Patent and Trademark Office*